United States Patent [19]

Kawamura et al.

[11] Patent Number: 5,508,185
[45] Date of Patent: Apr. 16, 1996

[54] LIPASE IMMOBILIZED ON A CHITOSAN CARRIER

[75] Inventors: Yoshihide Kawamura; Hiroaki Tanibe; Shigeyuki Imamura; Junko Harada, all of Shizuoka, Japan

[73] Assignee: Fuji Spinning Co., Ltd., Tokyo, Japan

[21] Appl. No.: 289,218

[22] Filed: Aug. 11, 1994

[30] Foreign Application Priority Data

Sep. 27, 1993 [JP] Japan .................................. 5-262979

[51] Int. Cl.$^6$ ........................... C12N 11/00; C12N 11/10
[52] U.S. Cl. ............................................. 435/178; 435/174
[58] Field of Search ...................................... 435/174, 178

[56] References Cited

FOREIGN PATENT DOCUMENTS

| | | |
|---|---|---|
| 61-40337 | 2/1986 | Japan . |
| 61-76504 | 4/1986 | Japan . |
| 62-134090 | 6/1987 | Japan . |
| 1153090 | 6/1989 | Japan . |
| 4287689 | 12/1990 | Japan . |
| 3290188 | 12/1991 | Japan . |
| 4335893 | 11/1992 | Japan . |

OTHER PUBLICATIONS

"Immobilized Lipase Reactors for Modification of Fats and Oils—A Review", Journal of American Oil Chemist's Society, vol. 67, No. 12 (Dec. 1990).

Primary Examiner—David M. Naff
Assistant Examiner—Deborah K. Ware
Attorney, Agent, or Firm—Birch, Stewart, Kolasch & Birch

[57] ABSTRACT

An enzyme immobilizing carrier is produced by dissolving low-molecular weight chitosan in an aqueous acid solution and dropping the solution into a basic solution to produce regenerated porous chitosan in particles, reacting the regenerated porous chitosan in particles with the glycidyl ether of an aliphatic polyalcohol, and reacting further the resulting chitosan with the acid halide or acid anhydride of a higher fatty acid in a polar organic solvent. An enzyme and a polyfunctional cross-linking agent are reacted with the carrier to covalently immobilize the enzyme on the carrier. In a preferred embodiment, the enzyme is lipase and the carrier is produced by introducing the glycidyl ether of an aliphatic polyalcohol at 0.01 to 0.4 mole to 1 mole of the pyranose ring residue of the chitosan and by introducing a higher fatty acid having a total carbon number of 6 to 20 at 0.05 to 1 mole to 1 mole of the pyranose ring residue of the chitosan.

9 Claims, 12 Drawing Sheets

LIPASE IMMOBILIZED ON A CHITOSAN CARRIER

BACKGROUND OF THE INVENTION

1. Field of the Invention

The present invention relates to a method for producing an enzyme immobilizing carrier using regenerated porous chitosan in particles. The enzyme immobilizing carrier in accordance with the present invention is preferably used as a carrier for immobilizing a variety of enzymes that require carriers having hydrophobic groups.

Furthermore, the present invention relates to an immobilized lipase having excellent catalytic activity in the hydrolysis, synthesis or exchange reaction of ester bonds, where the enzyme is used in an organic solvent. More particularly, the present invention is to provide an immobilized lipase capable of asymmetric synthesis at a higher efficiency than free lipase, in an organic synthesis via the exchange reaction of a variety of esters.

2. Prior Art

It is known that cross-linked products of regenerated porous chitosan in particles are used extensively as enzyme immobilizing carriers.

The advantages of regenerated porous chitosan in particles include that the material is from a natural origin so it is quite safe; that larger pores are more uniformly present from the surface to the inside of the carrier when chitosan is used as a carrier than synthetic resin carriers, thus providing greater substrate diffusibility; that highly reactive amino groups convenient for immobilizing enzymes via covalent bonding are disposed within the molecule; and that chitosan itself has a higher affinity with the enzyme so that a higher amount of the enzyme may be immobilized onto chitosan.

Carriers of regenerated and cross-linked chitosan in particles, which is regenerated polysaccharide, have advantages, in that the stability thereof in an organic solvent is very high, in addition to the hydrophilicity and porosity of the products. However, the products have drawbacks, in view of their potency to express enzyme activity because the carriers of regenerated porous chitosan that is cross-linked with polyfunctional reagents are highly hydrophilic. Such carriers, when used for proteases and enzymes catalyzing carbohydrates and for the group of enzymes whose substrates are hydrophobic substances like lipid, have reduced expressed enzyme activity, since proteases and enzymes catalyzing carbohydrates require a certain degree of hydrophobicity for the carrier.

Japanese Patent Publication No. Sho 63-54285 discloses that porous chitosan in particles that is cross-linked with 4,4'-diphenylmethane diisocyanate or hexamethylene diisocyanate may be used to immobilize enzyme groups, such as proteases and enzymes catalyzing carbohydrates, that require a certain degree of hydrophobicity for the immobilizing carrier, and the group of enzymes whose substrates are hydrophobic substances such as lipids. However, the carriers have lower immobilized enzyme activity and lower expressed enzyme activity.

Recently, active research works has focused on the application of chitosan to enzymatic organic synthesis. This is due to the excellent characteristic properties of enzymes, wherein enzymes are reactive at ambient temperature and ambient pressure such that thermally unstable substances can be synthesized via enzymes, enzymatic reactions progress in an energy-saving manner without causing pollution, and enzymes have good reaction specificity, such as position specificity, substrate specificity and capability of asymmetric synthesis.

Enzyme reactions in organic solvents, in particular, are drawing attention, from the respect that hydrolases can be applied to various synthesis and transition reactions. Compared with other enzymes, many lipid hydrolases, such as lipases are so highly resistant to organic solvents that such lipases can facilitate reactions for ester exchange and ester synthesis at a high efficiency. Thus, extensive research work has been conducted. Because the production and purification of lipases demand laborious work, however, the development of an immobilized lipase of a higher efficiency has been an issue of importance for the industrial application of lipase.

A review of lipase immobilization is found in "Journal of American Oil Chemist's Society", Vol.67, pp.890–910 (1990), where examples of representative lipase immobilizing carriers are illustrated, including inorganic carriers such as diamatoceous earth, silica, porous glass, etc.; various synthetic resins and synthetic resin ion exchangers; and natural polysaccharide carriers such as cellulose and cross-linked dextrin introduced with ion exchange groups. According to this reference, it is reported that these carriers are grouped as either hydrophilic carriers and hydrophobic carriers, and that lipase immobilized on a hydrophobic carrier such as synthetic resin expresses a higher ester exchange activity than lipase immobilized on a hydrophilic carrier.

An example of a lipase immobilized onto a synthetic resin ion exchanger is disclosed in Japanese Patent Laid-open No. Hei 4-287689. According to this reference, lipase from Pseudomonas immobilized on Amberlite XAD-2 exerts an activity for the ester exchange reaction between acetate vinyl monomer and α-D,L-phenylethyl alcohol. Although such synthetic resin ion exchanger has higher hydrophobicity as a carrier, the exchanger has drawbacks such as solubilization of the residual monomers and swelling of the resin when the immobilized lipase is used for an enzyme reaction in an organic solvent, although such use is important for an immobilized lipase.

As a method for immobilizing lipase, alternatively, the treatment of lipase with phospholipid or fatty acid is reported. For immobilizing lipase, methods for treating an immobilizing carrier with phospholipid or fatty acid are disclosed in Japanese Patent Laid-open No. Sho 62-134090, Japanese Patent Laid-open No. Hei 1-153090, and Japanese Patent Laid-open No. Hei 4-335893. According to any of the methods disclosed therein, phospholipid or fatty acid immobilized onto an immobilizing carrier via adsorption or hydrophobic bonding is desorbed from the carrier during the use of the carrier, leading to a lower efficiency.

OBJECT AND SUMMARY OF THE INVENTION

An object of the present invention is to provide an enzyme immobilizing carrier having excellent immobilized enzyme activity and expressed enzyme activity for an enzyme group requiring hydrophobicity for the immobilizing carrier.

Another object of the present invention is to provide an immobilized lipase using the enzyme immobilizing carrier described above, the immobilized lipase being suitable for catalytic activity in the hydrolysis, synthesis and exchange reaction of ester bonds in an organic solvents and also being capable of facilitating ester exchange reaction at a higher efficiency.

The novel enzyme immobilizing carrier produced according to the present invention comprises a regenerated porous chitosan derivative in particles, where the amino groups and the hydroxyl groups of regenerated porous chitosan in particles are partially or wholly substituted with a higher fatty acid.

The enzyme immobilizing carrier in accordance with the present invention is produced by dissolving low-molecular weight chitosan in an aqueous acid solution and dropping the resulting solution into a basic solution to obtain regenerated porous chitosan in particles, reacting the regenerated porous chitosan in particles with a glycidyl ether of an aliphatic polyalcohol to obtain a cross-linked regenerated porous chitosan and thereafter reacting the cross-linked regenerated porous chitosan with an acid anhydride or acid halide of a higher fatty acid in a solvent. The enzyme immobilizing carrier produced according to the present invention has higher immobilized enzyme activity and expressed enzyme activity for the enzyme group requiring hydrophobicity for the immobilizing carrier.

Still furthermore, the present invention relates to an immobilized lipase with lipid hydrolysis activity of 0.01 to 2 U/mg per dry weight of the immobilized lipase, produced by dissolving low-molecular weight chitosan in an aqueous acid solution, dropping the solution into a basic solution thereby producing regenerated porous chitosan in particles, introducing a glycidyl ether of an aliphatic polyalcohol into the regenerated porous chitosan at a ratio of 0.01 to 0.4 mole per 1 mole of the pyranose ring residue of the chitosan to obtain a cross-linked regenerated porous chitosan, introducing a higher fatty acid of C6 to C20 in total at a ratio of 0.05 to 1 mole per 1 mole of the pyranose ring residue of the chitosan, and introducing a lipase, wherein the lipase is immobilized via covalent bonding. The lipid hydrolysis activity is herein designated as follows. Using an acetone solution containing 300 mM monolaurin and 2% water as a substrate solution, lipase is reacted with the solution at 37° C. for 15 minutes as shown in the Examples. When 1 μmol of glycerol is produced for 1 minute, the amount of the lipase is designated 1 U.

DETAILED DESCRIPTION OF THE PREFERRED EMBODIMENTS

Figure 1:
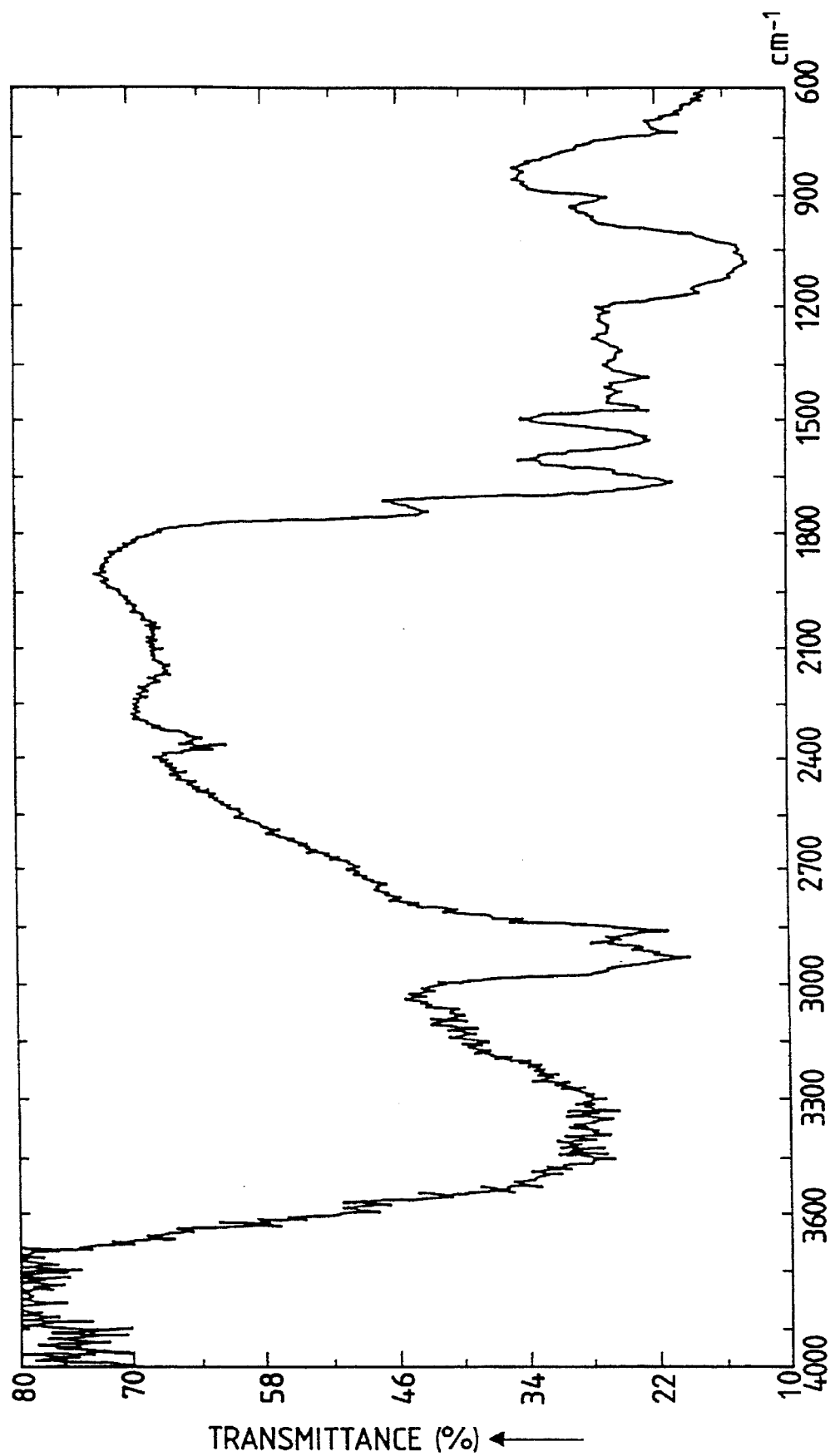
FIG. 1 shows the spectrograph of the enzyme immobilizing carrier after the introduction of a higher fatty acid obtained in Example 1 and analyzed by a Fourier Transform Infrared spectrophotometer.

The regenerated porous chitosan in particles can be produced by the method disclosed in Japanese Patent Publication No. Hei 1-16420 as follows. The regenerated chitosan is produced by dissolving low-molecular weight chitosan having an average molecular weight range of 10,000 to 230,000 in an aqueous acid solution, and dropping the solution into a basic solution, thereby solidifying and regenerating porous chitosan.

The cross-linking reaction of the regenerated porous chitosan in particles with the glycidyl ether of an aliphatic polyalcohol and the subsequent reaction with the acid halide or acid anhydride of a higher fatty acid are performed as follows.

Use is made of regenerated porous chitosan in particles that are preliminarily cross-linked prior to the reaction for introducing a higher fatty acid, as described below, since non-crosslinked regenerated porous chitosan in particles may dissolve in fatty acids and in organic acids generated in the reaction for introducing a higher fatty acid.

As disclosed in Japanese Patent Laid-open No. Hei 3-290188, the cross-linking reaction of the regenerated porous chitosan in particles is via a reaction of a glycidyl ether of an aliphatic polyalcohol.

The glycidyl ether of an aliphatic polyalcohol as the cross-linking agent to be used in the cross-linking reaction of the present invention, includes, for example, ethylene glycol diglycidyl ether or polyethylene glycol diglycidyl ether, having a dimethylene ether repeating number of 1 to 22; polypropylene glycol diglycidyl ether having a propylene ether repeating number of 1 to 66; glycerol polyglycidyl ether having 2 to 3 glycidyl ethers and the like. Examples of polyethylene glycol diglycidyl ether include ethylene glycol diglycidyl ether and diethylene glycol diglycidyl ether, etc.; examples of polypropylene glycol diglycidyl ether include propylene glycol diglycidyl ether and dipropylene glycol diglycidyl ether, etc.; examples of glycerol polyglycidyl ether include glycerol diglycidyl ether; and glycerol triglycidyl ether.

The reaction for introducing the glycidyl ether of an aliphatic polyalcohol into the regenerated porous chitosan in particles progresses under gentle agitation when the glycidyl ether of an aliphatic polyalcohol is at a concentration of 0.005 to 2 epoxy equivalents/liter and liquid volume of 1 to 5 fold that of the carrier volume, reaction temperature of 20° to 90° C., and reaction time for 1 to 24 hours.

When the regenerated porous chitosan in particles is used to prepare a carrier for lipase immobilization in accordance with the present invention, the glycidyl ether of an aliphatic polyalcohol is preferably introduced into the regenerated porous chitosan at a ratio of 0.01 to 0.4 mole per 1 mole of the pyranose ring residue of the chitosan during the cross-linking reaction of the regenerated porous chitosan.

If the amount of the glycidyl ether introduced is below 0.01 mole per 1 mole of the pyranose ring residue of the chitosan, the immobilized lipase is distinctively shrunken during dehydration and drying of the immobilized lipase for use in an organic solvent, resulting in a lower lipase activity for ester exchange reaction. Alternatively, it is difficult and impractical to increase the amount of the ether above 0.4 mole per 1 mole of the pyranose ring residue of the chitosan, and in such case, a decrease of activity is observed, disadvantageously.

Subsequently, the acid halide or acid anhydride of a higher fatty acid is introduced into the cross-linked regenerated porous chitosan in particles via covalent bonding.

The water contained in the cross-linked regenerated porous chitosan in particles, is sufficiently removed in a polar organic solvent. Such polar organic solvent includes, for example, dioxane, ethanol, isopropyl alcohol, dimethylformamide, dimethylacetamide, dimethylsulfoxide, pyridine and the like. For the subsequent introduction of the higher fatty acid, use may be made of a mixed solvent of these polar organic solvents with a non-polar organic solvent such as hexane, methylene chloride, chloroform, etc. Among these solvents, a solvent that is inactive to the acid anhydride or acid halide of a higher fatty acid may be appropriately selected. For a highly reactive substance such as acid halide, preference is given to the use of, for example any one of dioxane, dimethylformamide and dimethylacetamide or a mixture thereof.

The higher fatty acid to be used in accordance with the present invention is preferably a fatty acid, saturated or unsaturated, having a carbon number at which the hydrocarbon is hydrophobic. The carbon number is generally C6 to C20 in total.

Use may be made of the acid anhydride of a higher fatty acid, or the acid halide thereof, such as acid chloride or acid bromide. Preferably, the acid anhydride is, for example, lauric anhydride, myristic anhydride, palmitic anhydride, stearic anhydride, oleic anhydride, etc.; the acid halide is preferably, for example, lauroyl chloride, myristoyl chloride, palmitoyl chloride, stearoyl chloride, oleyl chloride, etc. The acid halide is more preferably used than the acid anhydride, since the amount of fatty acid introduced with the acid halide is larger than the amount introduced with the acid anhydride.

The reaction for introducing a higher fatty acid progresses under gentle agitation when the higher fatty acid is at a concentration of 10 to 1,000 mmol/liter and liquid volume of 1 to 5 fold that of the carrier volume, reaction temperature of 10° to 70° C., and reaction time of 1 to 24 hours.

When a deoxidizer is added for the purpose of removing the fatty acids or the inorganic acids generated during the reaction, any general deoxidizers dissolvable in the reaction solvent may be used without specific limitation. Triethylamine or pyridine is preferable.

When the cross-linked regenerated porous chitosan is used as a carrier for immobilizing lipase, the cross-linked regenerated porous chitosan is preferably modified with a higher fatty acid at a ratio of 0.05 to 1 mole per 1 mole of the pyranose ring residue of the chitosan.

If the amount of higher fatty acid introduced is below 0.05 mole, the lipid hydrolysis activity and ester exchange activity are extremely reduced, leading to a decrease in the ratio of expressed enzyme activity lipid hydrolysis activity. In such case, the immobilization procedure is useless. The ratio is improved by increasing the amount of the introduction of higher fatty acid, introduced. However, if the amount of higher fatty acid is above 1 mole, the ratio is close to saturation, so that the effect of the increase in the introduction cannot be observed.

Explanation will now follow with respect to the immobilized lipase produced by immobilizing lipase modified cross-linked regenerated porous chitosan carrier thus obtained.

In the following description, a carrier should be the modified cross-linked generated porous chitosan in particles obtained from the cross-linking reaction with the glycidyl ether of an aliphatic polyalcohol and the subsequent reaction for introducing the acid halide or acid anhydride of a higher fatty acid.

Lipase is immobilized subsequently onto the carrier produced. As such lipase, use is made of, for example, lipase from a microorganism, such as general Rhizopus, Aspergillus, Mucor, Pseudomonas, Penicillium, Chromobacterium, and Candida, and lipase from animal origin, such as panereas lipase. Preference is given to lipases from Chromobacterium and Pseudomonas, in particular.

The lipase is preferably at a high purity, and is preferably at a purity above 50% of the total protein. For lipase immobilization, the reaction temperature should be in a range with no occurrence of inactivation, and is for example 0° to 60° C., preferably 5° to 40° C. Also, an aqueous lipase solution should be in a pH range with no occurrence of enzyme inactivation preferably at pH 3 to 9.

Covalently bonding the enzyme to the carrier using a polyfunctional cross-linking agent significantly improves the tolerance of the immobilized lipase. As such polyfunctional cross-linking agent, illustration is made of for example glyoxal, glutaraldehyde, malonaldehyde, succinylaldehyde, bis-sulfosuccinimidyl suberate, dimethyl suberimidate, ethylene glycol bis-sulfosuccinimidyl succinate, dicyclohexylcarbodiimide, hexamethylene diisocyanate and the like. These agents may be used at 1.2 to 2 moles per 1 mole of lipase molecule.

These polyfunctional cross-linking agents may be preliminarily reacted with the carrier prior to introduction of the lipase, or may be reacted with the carrier after the lipase is hydrophobically bonded to the carrier. In accordance with the present invention, the immobilized enzyme produced by immobilizing lipase onto the carrier is designated "immobilized lipase".

In measuring the hydrolysis activity of lipase in water, the substrate lipid triglyceride generally does not dissolve in water. Therefore, the lipid is suspended in water by vigorously agitating a mixture of water and the lipid, or the lipid is prepared into an emulsion by adding a surfactant for dispersion of the lipid. When the immobilized lipase is introduced into water to measure the hydrolysis activity of the immobilized lipase, the microparticles of lipid cannot contact the immobilized lipase, leading to a far greater decrease in the ratio of expressed enzyme activity to lipase hydrolysis activity. Hence, lipid dissolved in an organic solvent should be used as an indicator of the activity of the immobilized lipase.

When the immobilized lipase is used in an organic solvent, the water contained in the immobilized lipase is removed with an organic solvent, and thereafter the immobilized lipase is dried in vacuum. The resulting dry immobilized lipase is subjected to reactions for ester hydrolysis, exchange and synthesis. The drying ratio of the dry immobilized lipase should be at a water content below 5%.

As shown in the Examples described below, the lipid hydrolysis activity of dry immobilized lipase is designated as follows. Using an acetone solution containing 300 mM monolaurin and 2% water as a substrate solution, lipase is reacted with the solution at 37° C. for 15 minutes as shown in the Examples described hereinafter. When 1 μmol of glycerol is produced for 1 minute, the amount of the lipase is designated 1 U.

Using the activity to hydrolyze lipid (monolaurin) in acetone as an indicator, an immobilized lipase with a lipid hydrolysis activity of 0.01 to 2 U/mg per dry weight of the immobilized lipase is preferable for the reactions of ester hydrolysis, exchange and synthesis. If the activity of the immobilized lipase is below 0.01 U/mg, the immobilized lipase is less stable and inactivated when stored in an organic solvent. Therefore, the activity is markedly decreased when measured after storage. Even if the amount of immobilized lipase is increased to yield an activity above 2 U/mg, the activity expressed is lower than that expected from the amount of the lipase; in other words, the activity does not increase relative to the increased amount of the lipase and it causes a loss of enzyme. Specifically preferable lipid hydrolysis activity is in a range of 0.1 U/mg to 1.5 U/mg.

The immobilized lipase thus obtained may be added to a substrate solution suspended in water or a buffer solution or to a substrate solution dissolved in an organic solvent, and used under agitation for mixing. Also, by passing a substrate solution through a reaction vessel such as a column preliminarily charged with the immobilized lipase, the reactions of ester hydrolysis, exchange and synthesis may be facilitated.

The present invention will now be explained in the Examples hereinbelow, but the present invention is not limited to such scope.

First, Examples 1 to 5 are illustrated so as to explain the method for producing an enzyme immobilizing carrier from the regenerated porous chitosan in particles, as well as the method for immobilizing glucoamylase and glucose isomerase onto the enzyme immobilizing carrier.

By using a Fourier Transform Infrared spectrophotometer (abbreviated as "FT-IR" hereinafter), it was confirmed by the following method that a higher fatty acid was introduced into the regenerated porous chitosan in particles after the reaction with the glycidyl ether of an aliphatic polyalcohol.

FT-IR analysis

The regenerated porous chitosan in particles having a higher fatty acid introduced therein was dried, ground and mixed with KBr. Based on the increase of absorption at 2850 $cm^{-1}$, 2925 $cm^{-1}$ and 1750 $cm^{-1}$ the introduction of a higher fatty acid was confirmed by FT-IR, Type JIR-AQS 20M/FX6160 (manufactured by JEOL Ltd.).

The activity of an enzyme solution, the immobilized enzyme activity and expressed enzyme activity were measured by the following methods.

Measurement of the activity of aqueous glucoamylase solution

1. Soluble starch (manufactured by Matsutani Kagaku, Co., Ltd.; Pinedex #100 as product name) is dissolved in 0.1 mol/l acetate buffer solution, pH 4.5 to a 10% concentration. The resulting solution is designated "substrate solution".

2. To 0.2 ml of an aqueous glucoamylase solution is added 4 ml of the substrate solution, which is then stirred at 40° C. for 30 minutes.

3. The solution is boiled for 5 minutes.

4. The resulting solution is diluted 50-fold with pure water. Then, the glucose generated is analyzed and measured in mg by HPLC (high-performance liquid chromatography).

The activity for generating 10 mg glucose at 40° C. for 30 minutes is designated 1 U (unit), and is calculated according to the following formula.

Glucoamylase activity (U/ml · aqueous solution) =   (1)

$$\text{generated glucose} \times \frac{1}{10} \times \frac{1}{0.2}$$

Measurement of the expressed enzyme activity for the immobilized glucoamylase

1. Soluble starch (manufactured by Matsutani Kagaku, Co., Ltd.; Pinedex #100 as product name) is dissolved in 0.1 mol/l acetate buffer solution, pH 4.5 to a 10% concentration. The resulting solution is designated "substrate solution".

2. To 0.2 ml of immobilized glucoamylase is added 4 ml of the substrate solution, which is then stirred at 40° C. for 30 minutes.

3. After removing the immobilized glucoamylase from the solution, the remaining solution is boiled for 5 minutes.

4. The resulting solution is diluted 50-fold with pure water. Then, the glucose generated is analyzed and measured in mg by HPLC.

The activity for generating 10 mg glucose at 40° C. for 30 minutes is designated 1 U, and is calculated according to the following formula.

Expressed glucoamylase activity (U/ml · carrier) =   (2)

$$\text{generated glucose} \times \frac{1}{10} \times \frac{1}{0.2}$$

Measurement of the activity of aqueous glucose isomerase solution

1. Crystalline glucose is dissolved in an aqueous 2 mmol/l $MgSO_4$ solution to a 45% concentration, and is adjusted to pH 8.0 by using 1N NaOH. The resulting solution is used as a substrate solution.

2. To 0.2 ml of glucose isomerase solution is added 2 ml of the substrate solution, which is then stirred at 70° C. for 15 minutes.

3. The solution is boiled for 5 minutes.

4. The resulting solution is diluted 100-fold with pure water. Then, the fructose generated is analyzed and measured in mg by HPLC.

The activity for generating 1 mg fructose at 70° C. for 60 minutes is designated 1 U, and is calculated according to the following formula.

Glucose isomerase activity (U/ml · aqueous solution) =   (3)

$$\text{generated fructose} \times \frac{60}{15} \times \frac{1}{0.2}$$

Measurement of the expressed glucose isomerase activity for immobilized glucose isomerase 1. Crystalline glucose is dissolved in an aqueous 2 mmol/l $MgSO_4$ solution to a 45% concentration, and is adjusted to pH 8.0 by using 1N-NaOH. The resulting solution is used as a substrate solution.

2. To 0.2 ml of immobilized glucose isomerase is added 2 ml of the substrate solution, which is then stirred at 70° C. for 15 minutes.

3. After removing the immobilized glucose isomerase from the solution, the remaining solution is boiled for 5 minutes.

4. The resulting solution is diluted 100-fold with pure water. Then, the fructose generated is analyzed and measured in mg by HPLC.

The activity for generating 1 mg fructose for 60 minutes at 70° C. is designated 1 U, and is calculated according to the following formula.

$$\text{Expressed glucose isomerase activity (U/ml} \cdot \text{carrier)} = \text{generated fructose} \times \frac{60}{15} \times \frac{1}{0.2} \tag{4}$$

The immobilized enzyme activity glucoamylase or glucose isomerase was measured by the following method.

Measurement of the immobilized enzyme activity

1. The activity of an aqueous enzyme solution to be used in an immobilization procedure is measured by the method described above. The activity measured is defined as A (U/ml).

2. The activity of an aqueous enzyme solution after the immobilization procedure is measured by the method described above. The activity measured is defined as B(V/ml water solution). Provided that the volume of the aqueous enzyme solution used in the immobilization procedure is defined as X (ml) and the volume of the immobilizing carrier is defined as V (ml), the immobilized enzyme activity is calculated by the following formula.

$$\text{The immobilized enzyme activity (U/ml} \cdot \text{carrier)} = \frac{(A - B) \times X}{V} \tag{5}$$

EXAMPLE 1

Chitosan (70 g) having a deacetylation degree of 80% and an average molecular weight of 48,000 was dissolved in an aqueous 3.5% acetate solution (930 g). The aqueous solution was dropped into a solidifying solution composed of 7% sodium hydroxide, 20% ethanol and 73% water, to solidify and regenerate the chitosan. The resulting chitosan was sufficiently washed in water to neutral pH to obtain wet regenerated porous chitosan in particles (500 ml) of an average particle size of 0.1 mm. To the resulting regenerated porous chitosan in particles (500 ml) were added 500 ml water and 3.6 g ethylene glycol diglycidyl ether for cross-linking at 60° C. for 1 hour. After completion of the reaction, the product was sufficiently washed in water to obtain cross-linked regenerated porous chitosan in particles.

Subsequently, the water contained in the cross-linked regenerated porous chitosan in particles was sufficiently removed with dioxane. To 200 ml of the cross-linked regenerated porous chitosan in particles was added a solution of stearoyl chloride (10 g) and triethylamine (2.25 g) dissolved in dioxane (200 ml) (the concentration of stearoyl chloride was 165 mmol/l), which was stirred at 40° C. for 10 hours. After removing the remaining reaction solution, the product was washed in dioxane, followed by removal of the dioxane with pure water to obtain an enzyme immobilizing carrier (Carrier A). The carrier was analyzed by FT-IR, and the results are shown in FIG. 1. Consequently, the increase in the absorption of methylene at 2850 cm$^{-1}$ and 2925 cm$^{-1}$ was confirmed together with the increase in the absorption of ester at 1750 cm$^{-1}$ indicating that the stearoyl was introduced.

Onto Carrier A was immobilized glucoamylase by the following method. To Carrier A (1 ml) was added an aqueous 5% glutaraldehyde solution (5 ml), which was stirred at room temperature for 1 hour. After removing the aqueous glutaraldehyde solution after the reaction, glucoamylase (manufactured by Amano Pharmaceutical Co., Ltd.; NL 4.2 as product name) was diluted 10-fold with pure water. The resulting aqueous enzyme solution (5 ml) was added to the carrier, and stirred at room temperature for 2 hours. After removing the aqueous enzyme solution after the reaction, the product was sufficiently washed in pure water to obtain immobilized glucoamylase. The immobilized enzyme activity and expressed enzyme activity of the glucoamylase immobilized carrier were 1660 U/ml.carrier and 165 U/ml.carrier, respectively.

COMPARATIVE EXAMPLE

The water contained in regenerated porous chitosan (500 ml in wet state) in particles having an average particle size of 0.1 mm, obtained by the same method as in Example 1, was sufficiently removed with dimethylformamide. To 500 ml of the regenerated porous chitosan in particles were added dimethylformamide (500 ml) and 4,4'-diphenylmethane diisocyanate (50 g), for reaction at room temperature for 2 hours. The unreacted diphenylmethane diisocyanate was removed with dimethylformamide, and the resulting product was sufficiently washed in water to obtain an enzyme immobilizing carrier (400 ml; Carrier B).

Onto the enzyme immobilizing carrier was immobilized glucoamylase by the same method as in Example 1. The immobilized enzyme activity and expressed enzyme activity of the glucoamylase immobilized carrier were 1540 U/ml.carrier and 100 U/ml.carrier, respectively.

As apparently shown in the results of Example 1 and Comparative Example, the method of the present invention was excellent in the immobilized enzyme activity and expressed enzyme activity for the enzyme, compared with the conventional method.

EXAMPLE 2

Figure 2:
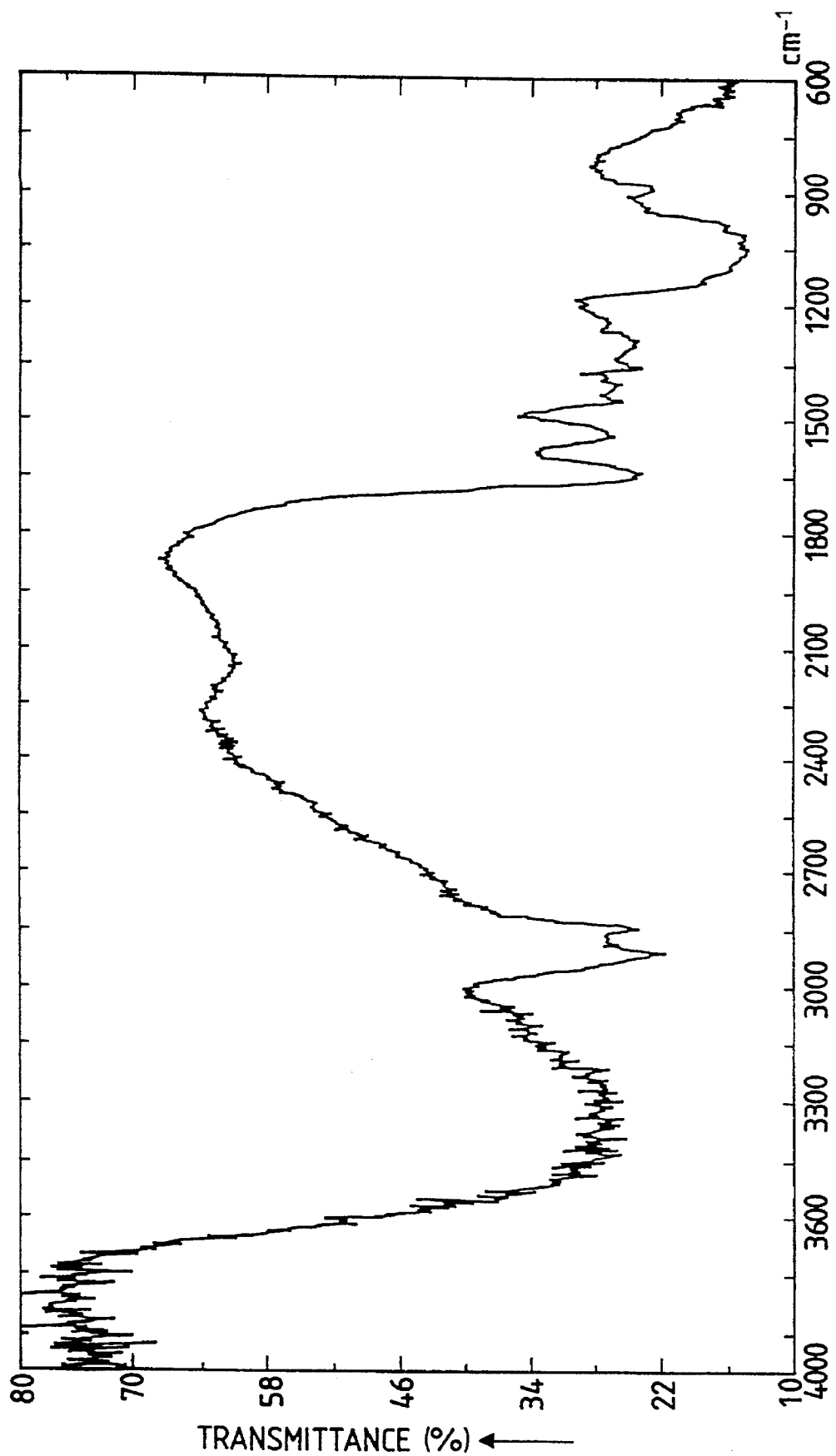
FIG. 2 shows the spectrograph of the enzyme immobilizing carrier after the introduction of a higher fatty acid obtained in Example 2 and analyzed by a Fourier Transform Infrared spectrophotometer.

The water contained in the cross-linked regenerated porous chitosan in particles, obtained by the same method as in Example 1, was sufficiently removed with dimethylformamide. To the cross-linked regenerated porous chitosan in particles (200 ml) was added a solution of myristic anhydride (17.5 g) dissolved in dimethylformamide (200 ml) (the concentration of myristic anhydride was 20 mmol/l), which was stirred at 40° C. for 10 hours. After removing the remaining reaction solution, the product was washed in dimethylformamide, followed by removing the dimethylformamide with pure water to obtain the enzyme immobilizing carrier (Carrier C). The carrier was analyzed by FT-IR, and the results are shown in FIG. 2. Consequently, the increase in the absorption of methylene at 2850 cm$^{-1}$ and 2925 cm$^{-1}$ was confirmed, indicating the myristoyl was introduced.

EXAMPLE 3

The water contained in the cross-linked regenerated porous chitosan in particles, obtained by the same method as in Example 1, was sufficiently removed with dimethylformamide. To the cross-linked regenerated porous chitosan in particles (200 ml) was added a solution of stearoyl chloride (3 g) and triethylamine (0.68 g) dissolved in dimethylformamide (200 ml) (the concentration of stearoyl chloride was then 50 mmol/l), which was stirred at 40° C. for 10 hours.

Figure 3:
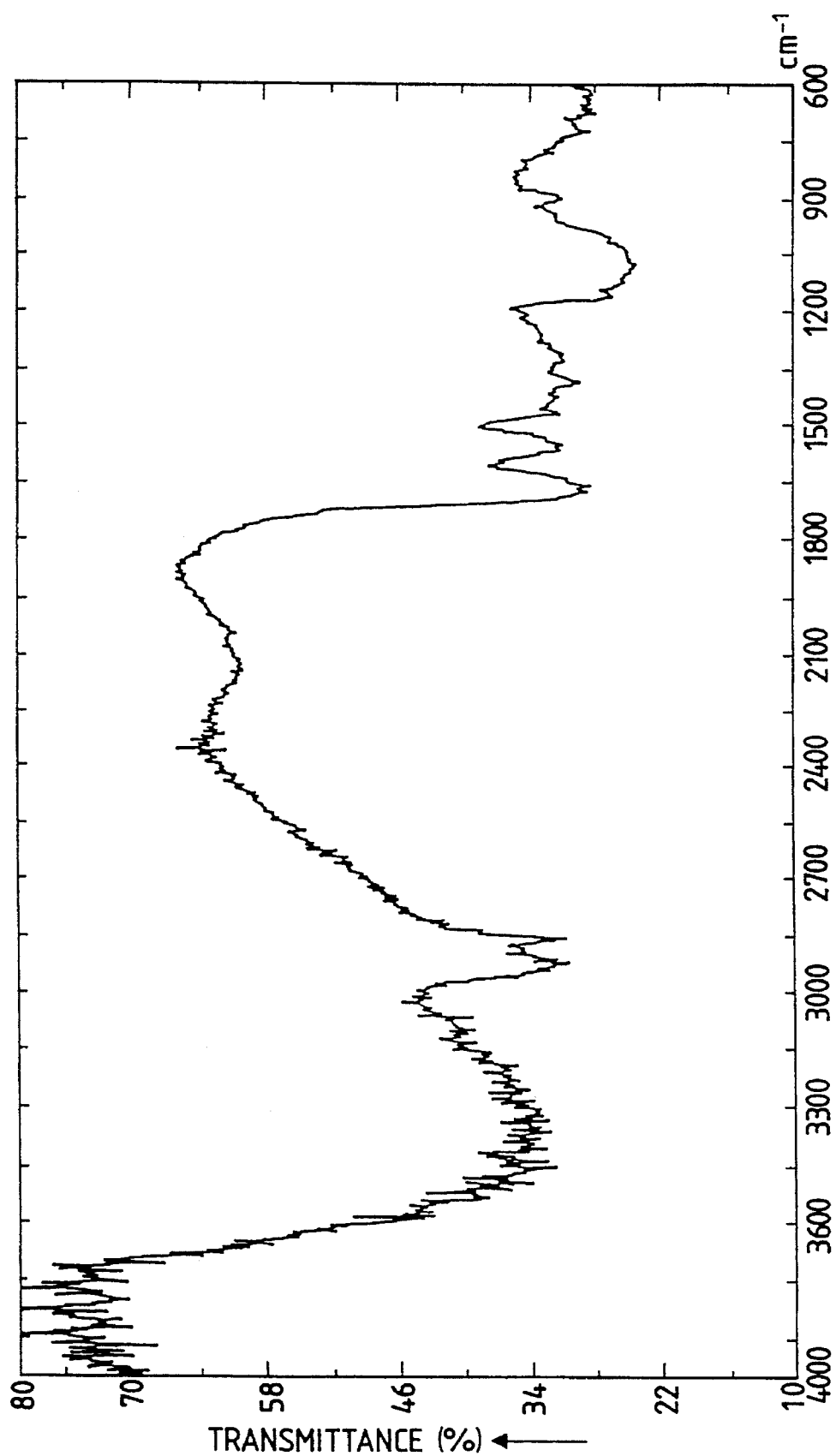
FIG. 3 shows the spectrograph of the enzyme immobilizing carrier after the introduction of a higher fatty acid obtained in Examples 3 and analyzed by a Fourier Transform Infrared spectrophotometer.

After removing the remaining reaction solution, the product was washed in dimethylformamide, followed by removing the dimethylformamide with pure water to obtain the enzyme immobilizing carrier (Carrier D). The carrier was analyzed by FT-IR, and the results are shown in FIG. 3. Consequently, the increase in the absorption of methylene at 2850 cm$^{-1}$ and 2925 cm$^{-1}$ was confirmed, indicating that the stearoyl was introduced.

EXAMPLE 4

Figure 4:
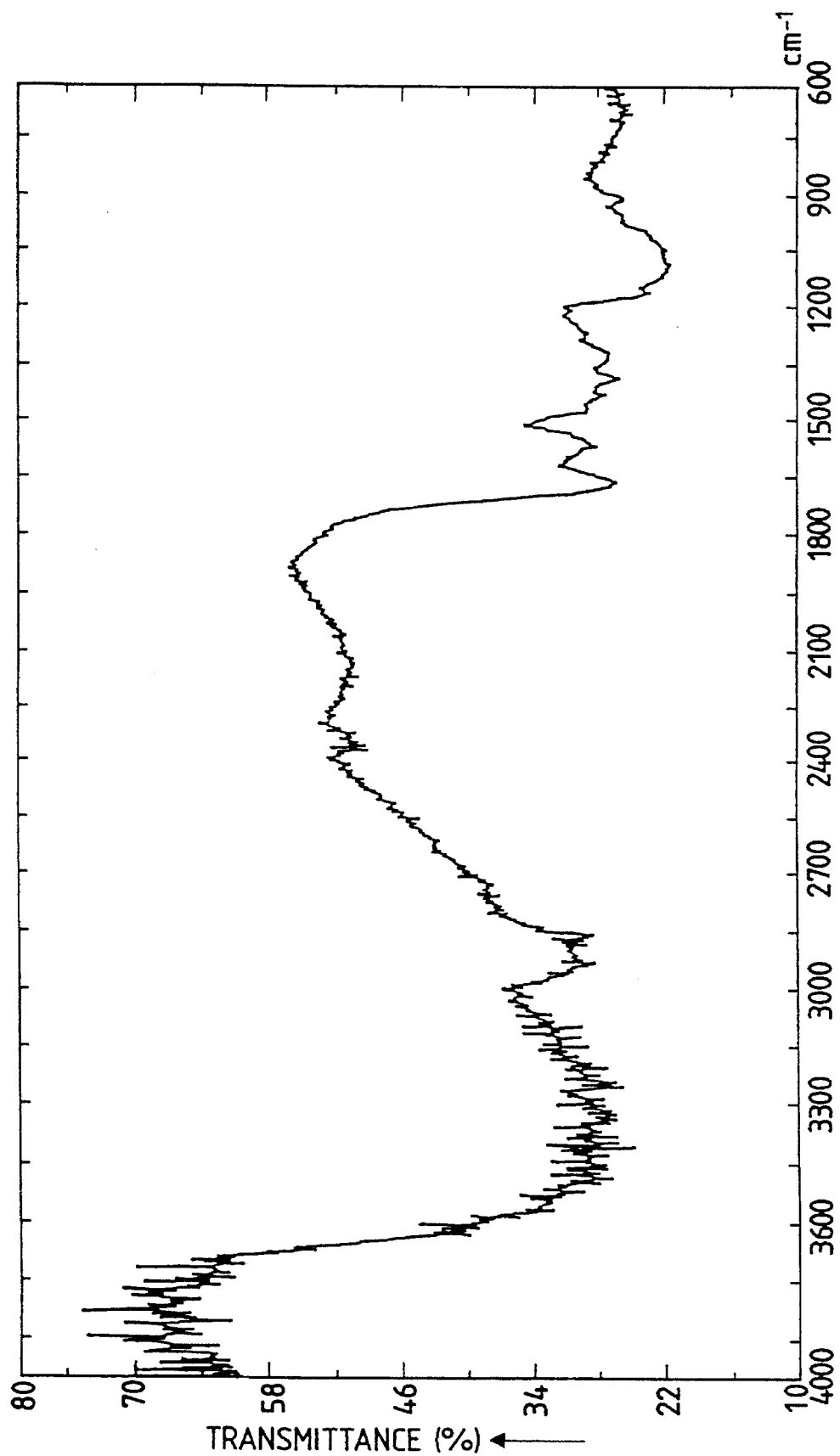
FIG. 4 shows the spectrograph of the enzyme immobilizing carrier after the introduction of a higher fatty acid obtained in Example 4 and analyzed by a Fourier Transform Infrared spectrophotometer.
Figure 5:
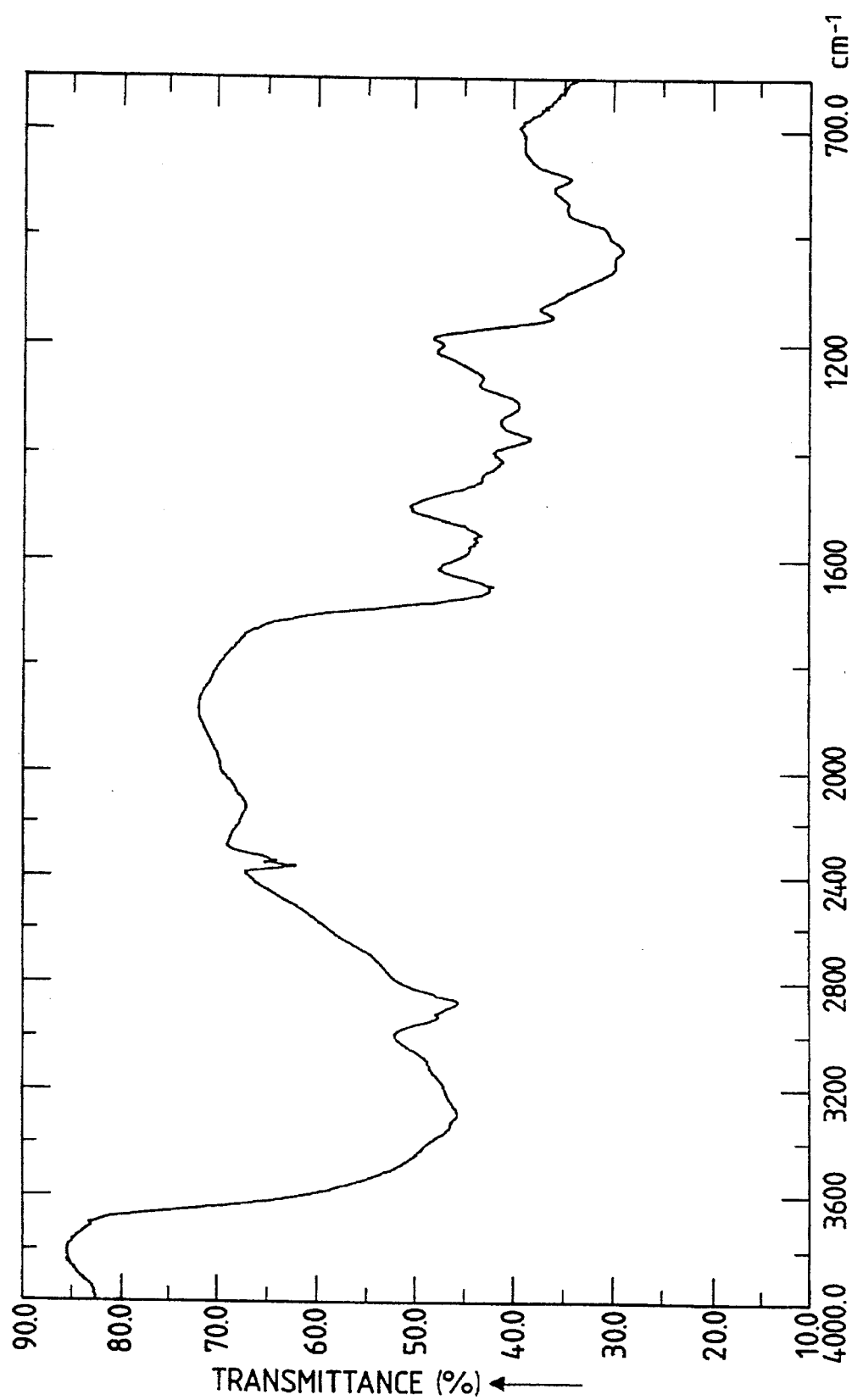
FIG. 5 shows the results of the analysis of the chitosan carrier L' by a Fourier Transform Infrared spectrophotometer.
Figure 6:
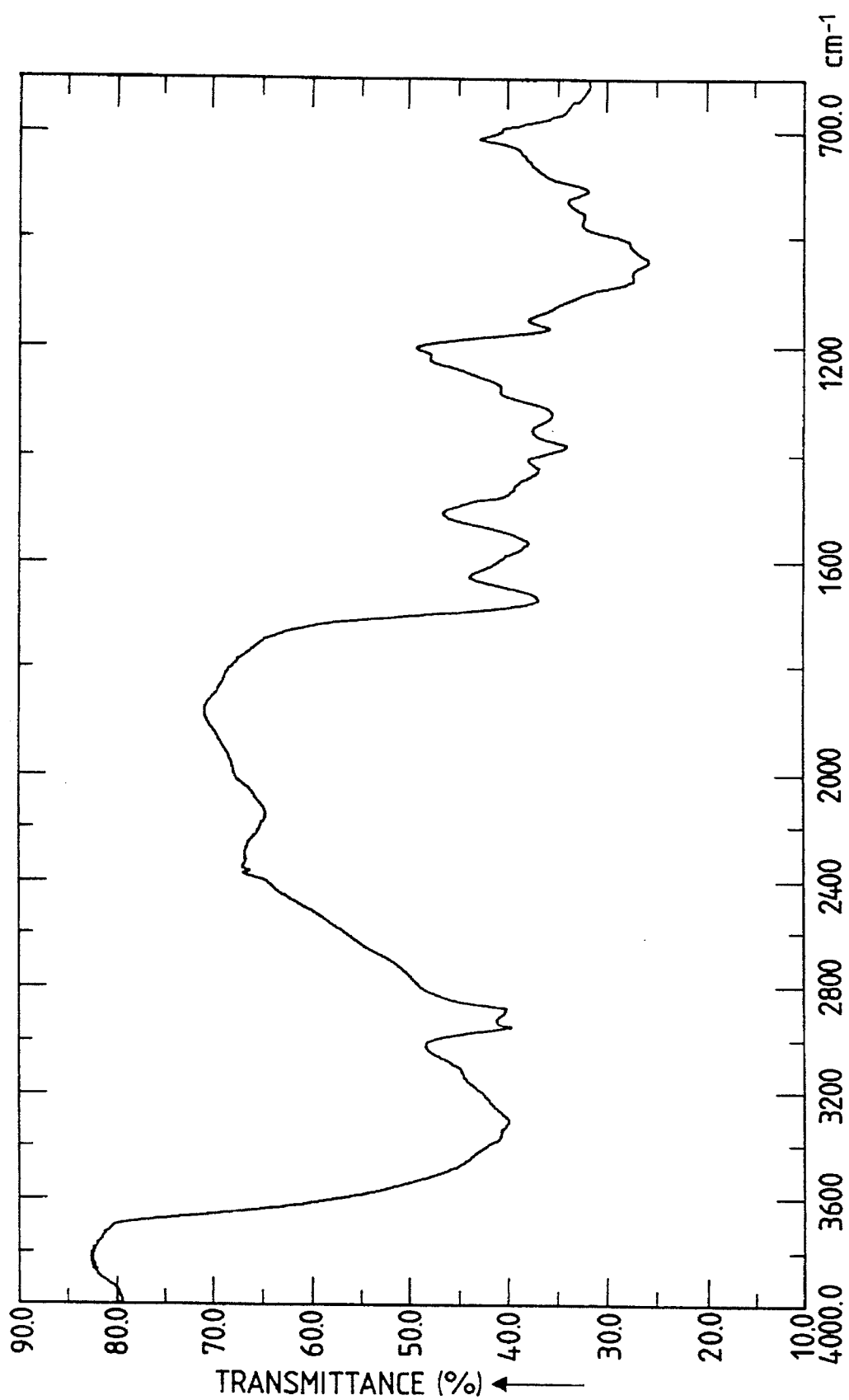
FIG. 6 shows the results of the analysis of the chitosan carrier M' by a Fourier Transform Infrared spectrophotometer.
Figure 7:
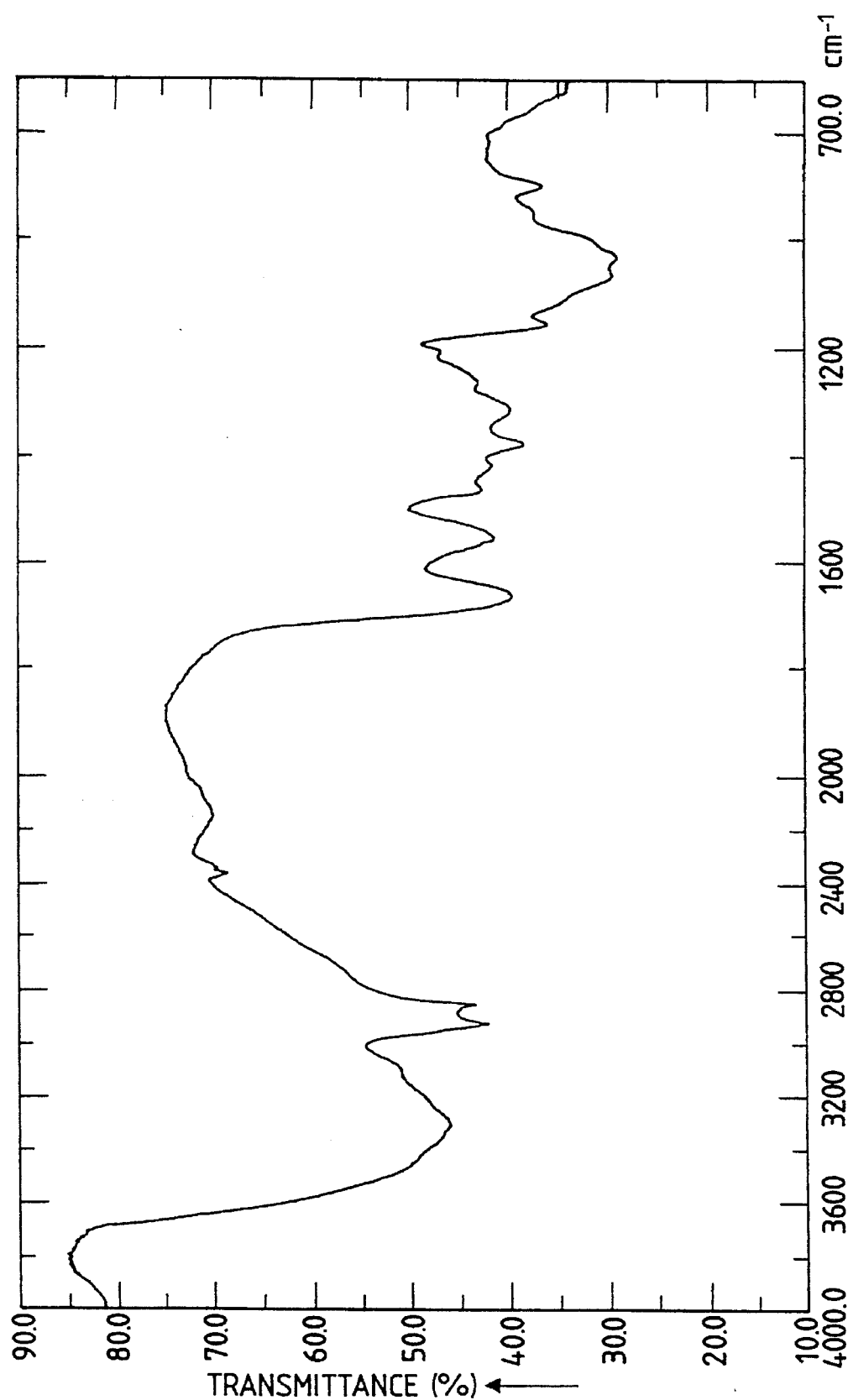
FIG. 7 shows the results of the analysis of the chitosan carrier N' by a Fourier Transform Infrared spectrophotometer.
Figure 8:
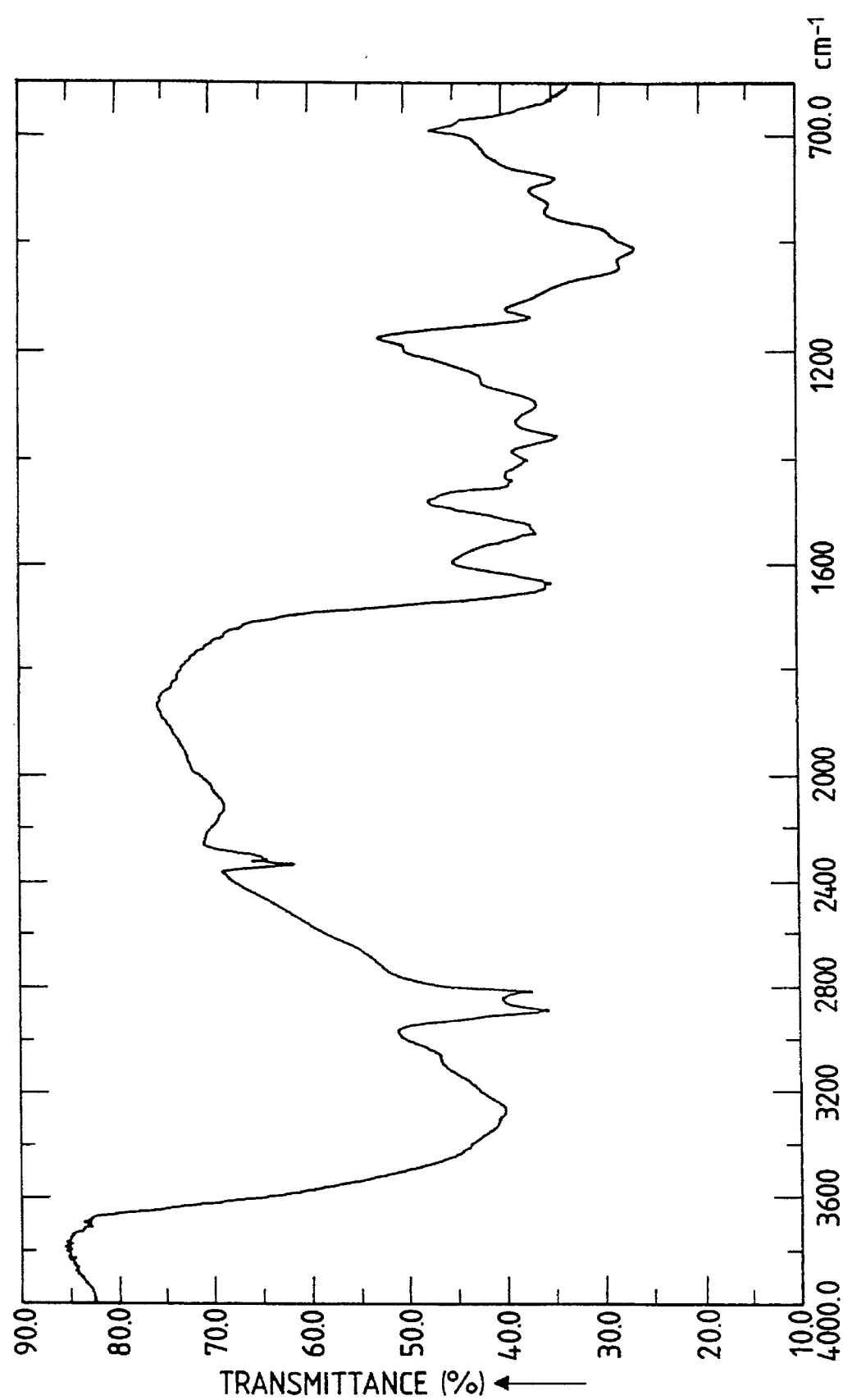
FIG. 8 shows the results of the analysis of the chitosan carrier O' by a Fourier Transform Infrared spectrophotometer.
Figure 9:
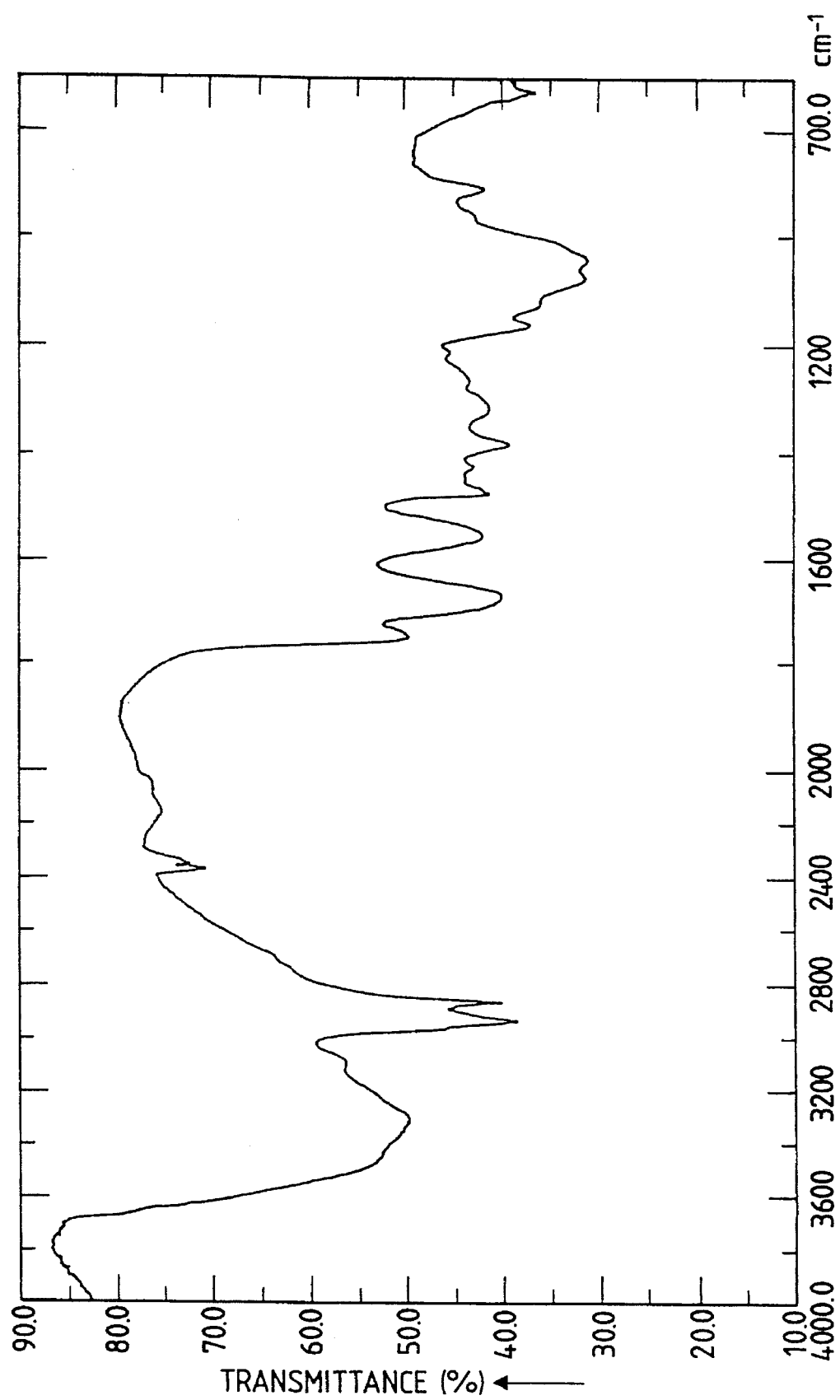
FIG. 9 shows the results of the analysis of the chitosan carrier P' by a Fourier Transform Infrared spectrophotometer.
Figure 10:
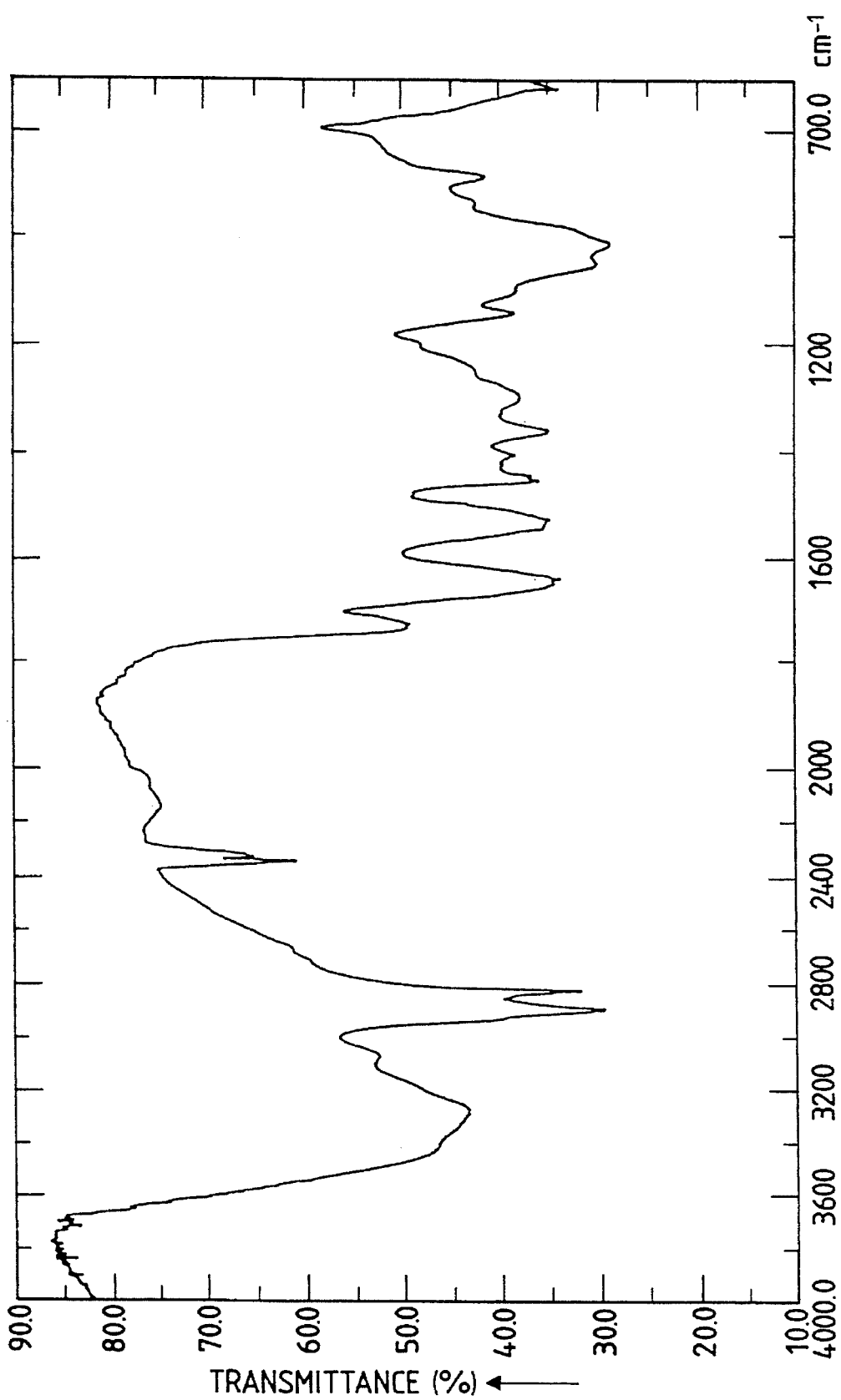
FIG. 10 shows the results of the analysis of the chitosan carrier Q' by a Fourier Transform Infrared spectrophotometer.
Figure 11:
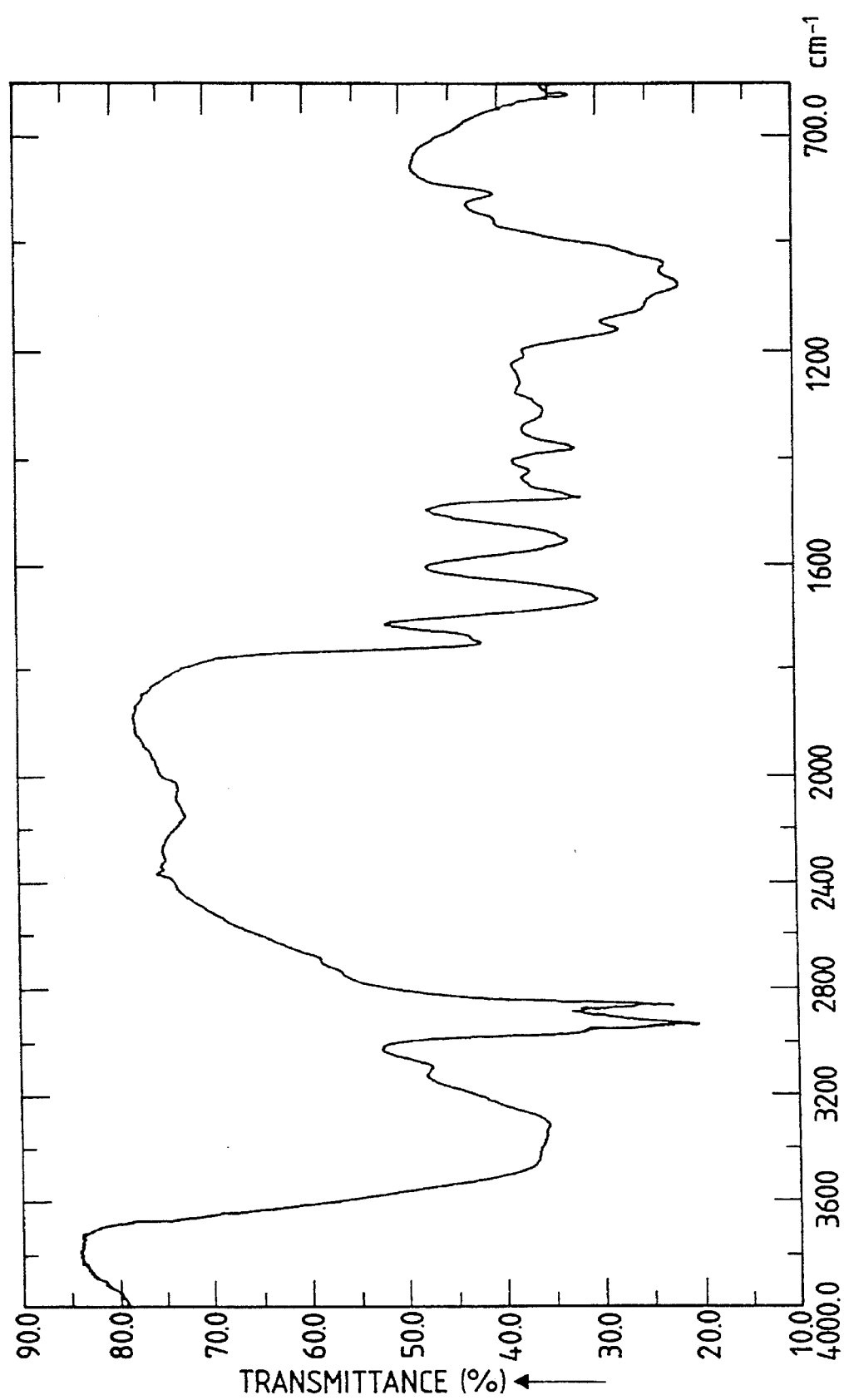
FIG. 11 shows the results of the analysis of the chitosan carrier R' by a Fourier Transform Infrared spectrophotometer.
Figure 12:
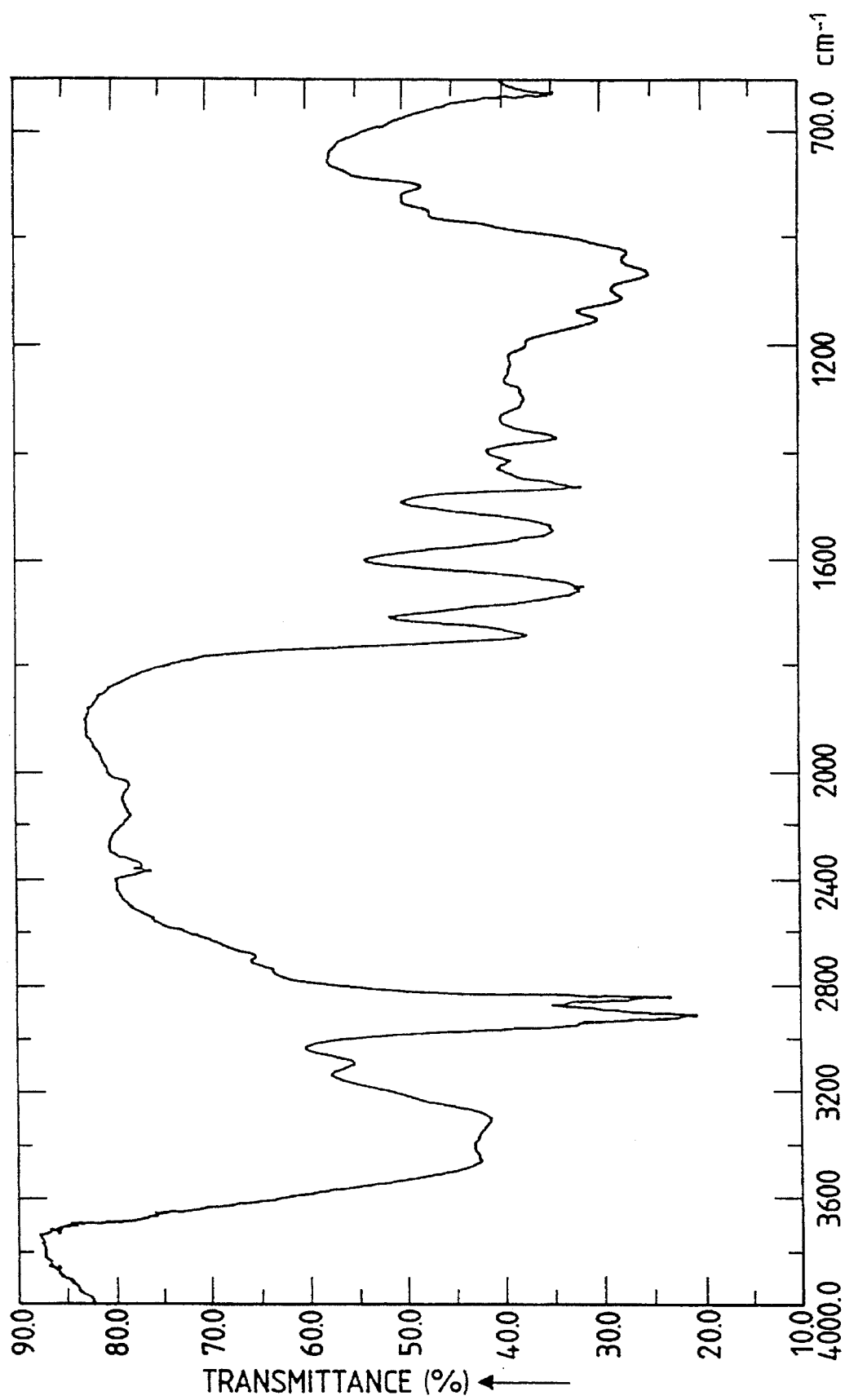
FIG. 12 shows the results of the analysis of the chitosan carrier S' by a Fourier Transform Infrared spectophotometer.

The water contained in the cross-linked regenerated porous chitosan in particles, obtained by the same method as in Example 1, was sufficiently removed with dimethylformamide. To the cross-linked regenerated porous chitosan in particles (200 ml) was added a solution of stearoyl chloride (1.22 g) and triethylamine (0.27 g) dissolved in dimethylformamide (200 ml) (the concentration of stearoyl chloride was then 20 mmol/l), which was stirred at 40° C. for 10 hours. After removing the remaining reaction solution, the product was washed in dimethylformamide, followed by removing the dimethylformamide with pure water to obtain the enzyme immobilizing carrier (Carrier E). The carrier was analyzed by FT-IR, and the results are shown in FIG. 4. Consequently, the increase in the absorption of methylene at 2850 cm$^{-1}$ and 2925 cm$^{-1}$ was confirmed, indicating that the stearoyl was introduced.

EXAMPLE 5

Onto each of the enzyme immobilizing carriers obtained in Example 1, Comparative Example, and Examples 2, 3 and 4 ie. Carriers A, B, C, D and E, was immobilized glucose isomerase by the following method. To 1 ml each of the enzyme immobilizing carriers was added an aqueous 5% glutaraldehyde solution (5 ml), which was stirred at room temperature for 1 hour. After removing the aqueous glutaraldehyde solution after the reaction, glucose isomerase in liquid (10 ml) (manufactured by Nagase Biochemicals, Ltd.; 5600 U/ml) was added to each of the carriers and stirred at room temperature for 2 hours. After removing the aqueous enzyme solution after the reaction, the product was sufficiently washed in pure water, to obtain immobilized glucose isomerase. The immobilized enzyme activity and expressed enzyme activity of the carriers were measured, and the results are shown in Table 1.

TABLE 1

| Samples | Ex. 1 Carrier A | Com. Ex. Carrier B | Ex. 2 Carrier C | Ex. 3 Carrier D | Ex. 4 Carrier E |
|---|---|---|---|---|---|
| Express enzyme activity (U/ml carrier) | 13200 | 11800 | 15300 | 17400 | 15200 |
| Immobilized enzyme activity (U/ml carrier) | 3320 | 2200 | 3410 | 3720 | 3520 |

As clearly shown in Table 1, the enzyme immobilizing carriers obtained by the present method, were excellent in immobilized enzyme activity and expressed enzyme activity.

Subsequently, Examples 6 to 10 illustrate an immobilized lipase produced by immobilizing lipase onto the enzyme immobilizing carriers obtained from the regenerated porous chitosan in particles. Using the test methods described below, various measurements were made.

1. Method for measuring the amount of the glycidyl ether of an aliphatic polyalcohol introduced into the regenerated porous chitosan in particles i) After the reaction of the glycidyl ether of an aliphatic polyalcohol with the regenerated porous chitosan in particles, the cross-linked regenerated porous chitosan was filtered off, and the remaining reaction solution was recovered.

ii) To the cross-linked regenerated porous chitosan was added pure water in the same volume as that of the cross-linked chitosan which was stirred at room temperature for 20 minutes, followed by washing. The cross-linked regenerated porous chitosan was filtered off, and the remaining solution was recovered. The procedure was repeated 4 times.

iii) The recovered remaining reaction solutions were concentrated under reduced pressure with a rotary evaporator until the water was sufficiently removed to dryness in evaporation.

iv) The residue glycidyl ether of the aliphatic polyalcohol was dissolved in tetrahydrofuran, for HPLC analysis. Another aqueous solution of glycidyl ether of the aliphatic polyalcohol was prepared prior to the reaction, and the solution was analyzed by HPLC.

v) The following formula is used to determine the amount of the ether introduced per pyranose ring residue.

$$\text{Introduced amount (mole)} = \frac{(A - B)}{WPE} \div \frac{C \times V}{M} \quad (6)$$

wherein

A=Amount of the glycidyl ether of an aliphatic polyalcohol charged (g)

B=Amount of the glycidyl ether of an aliphatic polyalcohol remaining after reaction (g)

WPE=Epoxy equivalent of the glycidyl ether of an aliphatic polyalcohol charged

N=Number of epoxy group of the molecule of the glycidyl ether of an aliphatic polyalcohol V=volume of regenerated porous chitosan in particles charged (ml)

C=Dry weight of 1 ml of the regenerated porous chitosan in particles (g/ml)

M=Molecular weight of pyranose ring residue.

2. Method for measuring the amount of a higher fatty acid introduced into the carrier i) The acid anhydride or acid halide of a higher fatty acid was added to the cross-linked regenerated porous chitosan in particles to concentrations of 20, 50, 100, 150, 300 and 500 mmol/l for reaction in a solvent. Then, the modified cross-linked regenerated porous chitosan was filtered off, and the remaining reaction solution was recovered.

ii) To the modified cross-linked regenerated porous chitosan in particles after the introduction of a higher fatty acid was added the same solvent of the same volume as used in the reaction, which was stirred at room temperature for 20 minutes, followed by washing. The modified cross-linked regenerated porous chitosan in particles was filtered off, and the remaining solution was recovered. The procedure was repeated twice.

iii) Subsequently, a reaction solvent containing 1,000 mmol/l triethylamine was added to the modified cross-linked regenerated porous chitosan in particles in the same volume as that of the modified carrier, which was stirred at room temperature for 30 minutes, followed by washing. The modified cross-linked regenerated porous chitosan in particles was filtered off, and the remaining solution was recovered.

vi) To the modified cross-linked regenerated porous chitosan in particles was added the solvent used for the reaction in the same volume as that of the modified carrier, which was stirred at room temperature for 20 minutes, followed by washing. The modified cross-linked regenerated porous chitosan in particles was filtered off, and the remaining solution was recovered. The procedure was repeated four times.

v) To the higher fatty acid and the acid anhydride or acid halide of the higher fatty acid, contained in the recovered remaining solutions, was added tetramethyl ammonium hydroxide as a methylating agent. The unreacted acid anhydride or acid halide of the higher fatty acid was analyzed and measured by thermolysis gas chromatography method using a thermolysis system Curie Point Pyrolyzer (Japan Analytical Industry, Co., Ltd.; Type JHP-3) and a gas chromatography system (manufactured by Shimadzu, Co.; Tyep GCMS-QP 2,000 GF).

vi) By subtracting the amount of unreacted acid anhydride or acid halide of the higher fatty acid from the charged amount of the acid anhydride or acid halide, the amount of the introduced higher fatty acid can be determined. By the following formula, the introduced amount of the higher fatty acid is calculated per glucosamine residue.

$$\text{Introduced amount (mole)} = \frac{(A-B)}{W} \div \frac{C \times V}{M} \quad (7)$$

wherein
A=Amount of the acid anhydride or acid halide of a higher fatty acid charged in weight (g)
B=Amount of the acid anhydride or acid halide of a higher fatty acid remaining after reaction (g)
W=Molecular weight of the acid anhydride or acid halide of a higher fatty acid
V=Volume of the cross-linked regenerated porous chitosan in particles charged (ml)
C=Dry weight of 1 ml of the cross-linked regenerated porous chitosan in particles (g/ml)
M = Molecular weight of pyranose ring residue.

vii) The modified carrier is dried and ground.

viii) To the ground carrier is added tetramethylammonium hydroxide as a methylating agent as in the above v), and the introduced amount of the higher fatty acid in the sample is determined by thermolysis gas chromatography.

Based on the results, the introduced amount of the higher fatty acid in the carrier is measured and determined by thermolysis gas chromatography.

3. Method for FT-IR analysis

A carrier, dried and ground, is diluted with KBr, and analyzed by FT-IR (Type JIR-DIAMOND 20, manufactured by JEOL, Ltd.). Based on the increase in the absorption of methylene at 2850 cm$^{-1}$ and 2925 cm$^{-1}$ and in the absorption of ester at 1750 cm$^{-1}$, the introduction of stearoyl is confirmed. 4. Method for preparing immobilized lipase i) A carrier (1 g in wet weight) is sampled.

ii) A given concentration of an aqueous lipase solution (1 ml), 1M phosphate buffer solution, pH 7.5 (0.5 ml) and pure water (23.5 ml) are mixed together. The resulting mixture solution is designated "enzyme solution" to which is added the carrier iii) So as to adsorb lipase onto the carrier, the solution is stirred at 37° C for 1 hour.

iv) The carrier is filtered off, which is then sufficiently washed in water.

v) 1M phosphate buffer solution, pH 7.5 (0.5 ml), pure water (24.25 ml) and an aqueous 1% glutaraldehyde solution (0.25 ml) are mixed together, and the resulting solution is designated "immobilizing solution".

vi) The carrier after lipase adsorption is added to the immobilizing solution, and stirred at 37° C. for 1 hour, to immobilize the lipase onto the carrier via covalent bonding.

vii) The carrier is filtered off, which is then sufficiently washed in water to obtain wet immobilized lipase.

viii) The water contained in the immobilized lipase is completely removed with acetone for dehydration, followed by drying in vacuum, to obtain dry immobilized lipase at a water content below 5%.

5. Method for measuring the lipid hydrolysis activity of free lipase i) An acetone solution (4.9 ml) is prepared, containing 306 mM monolaurin.

ii) To the solution is added aqueous 2 mg/ml lipase solution (0.1 ml) for reaction at 37° C. for 15 minutes. (The concentration of monolaurin then is 300 mM at a water content of 2%.)

iii) After the reaction, the solution (0.5 ml) and 0.2N HCl (0.5 ml) are mixed together and left to stand at 50° C. for 10 minutes to inactivate lipase, thereby yielding a lipid hydrolyzed solution.

iv) A test solution of the following composition is prepared;
50 mM Tris-HCl buffer (pH 7.5)
0.05% surfactant (Triton X-100, manufactured by Roam and Hers, Co., Ltd.)
1 mM MgCl$_2$
1 mM adenosine triphosphate
1 U/ml glycerol kinase
5 U/ml glycerophosphate oxidase
0.03% 4-amino antipyrine
0.03% 3,5-dimethoxy-N-ethyl-(2-hydroxy-3-sulfopropyl)-aniline, sodium salt
4.5 U/ml peroxidase.

v) The solution after the reaction with lipase is diluted 11-fold with 2% Triton X-100, and subsequently, the diluted solution (20 μl) is charged into the test solution (0.5 ml) described in iv) for color developing reaction at 37° C. for 10 minutes.

vi) After adding 0.5% sodium dodecyl sulfate (1 ml), the absorbance at 600 nm is measured.

vii) The lipid hydrolysis activity is determined by the following formula.

$$\text{Lipid hydrolysis activity of free lipase (U/mg)} = \quad (8)$$

$$\frac{\text{absorbance at 600 nm}}{7.2} \times$$

$$1.52 \times 11 \times 5 \times 2 \times \frac{1}{0.02} \times \frac{1}{15} \times \frac{1}{0.2}$$

6. Method for measuring the expressed hydrolysis activity of dry immobilized lipase i) To an acetone solution (5 ml) containing 300 mM monolaurin and 2% water is added dry immobilized lipase for reaction under stirring at 37° C. for 15 minutes.

ii) The immobilized lipase is filtered off, to obtain lipid hydrolyzed solution.

iii) By the same method as described in V) above in "5. Method for measuring the lipid hydrolysis activity of free lipase", the absorbance is measured.

iv) The activity is determined by the following formula.

$$\text{Expressed lipid hydrolysis activity of immobilized lipase (U/mg)} = \frac{\text{absorbance at 600 nm}}{7.2} \times 1.52 \times 11 \times 5 \times \frac{1}{0.02} \times \frac{1}{15} \times \frac{1}{10} \quad (9)$$

7. Method for measuring the ester exchange activity of free lipase i) A hexane solution containing 2.5% α-D, L-phenylethyl alcohol and 2% acetate vinyl monomer is prepared, which is then defined as substrate.

ii) Powdery lipase at an amount in weight corresponding to 5 U of hydrolysis activity is weighed, and is subsequently added to the substrate (2 ml) for stirring at 25° C. for 3 hours to facilitate ester exchange reaction.

iii) After the completion of the reaction, the lipase is immediately filtered off, and the reaction solution is cooled to −50° C. to terminate the reaction.

iv) Using a column for optical resolution (CHIRALCEL OB, manufactured by Daicell Chemical Industries, Ltd.), the composition of the reaction solution is analyzed by HPLC, to determine the decrease in the amount of α-L-phenylethyl alcohol (in μmol).

v) When free lipase acylates 1 μmol of α-L-phenylethyl alcohol at 25° C. per minute, the ester exchange activity is designated 1 U. The activity is determined by the following formula.

$$\text{Ester exchange activity of free lipase (U/mg)} = \frac{\Delta Q}{3 \times 60} \times \frac{1}{W} \quad (10)$$

wherein
ΔQ=the decrease in the amount of α-L-phenylethyl alcohol (in μmol).
W=free lipase required for the reaction (mg).

8. Method for measuring the expressed ester exchange activity of dry immobilized lipase i) After removing the water contained in wet immobilized lipase with acetone to dry the lipase in vacuum and further removing the acetone, dry immobilized lipase is obtained.

ii) A hexane solution containing 2.5% α-D, L-phenylethyl alcohol and 2% acetate vinyl monomer is prepared, which is then defined as the substrate.

iii) Powdery immobilized lipase at an amount in weight corresponding to 10 U of hydrolysis activity is weighed, and is subsequently added to the substrate (2 ml) for stirring at 25° C. for 3 hours to facilitate ester exchange reaction.

iv) After the completion of the reaction, the immobilized lipase is immediately filtered off, to terminate the reaction.

v) Using a column for optical resolution (CHIRALCEL OB, manufactured by Daicell Chemical Industries, Ltd.), the composition of the reaction solution is analyzed by HPLC, to determine the reduction of the amount of α-L-phenylethyl alcohol (in μmol).

vi) When free lipase acylates 1 μmol of α-L-phenylethyl alcohol at 25° C. per minute, the ester exchange activity is designated 1 U. The activity is determined by the following formula.

$$\text{Expressed ester exchange activity of dry immobilized lipase (U/mg)} = \frac{\Delta Q}{3 \times 60} \times \frac{1}{W} \quad (11)$$

wherein
ΔQ=the decrease in the amount of α-L-phenylethyl alcohol (in μmol).
W=dry immobilized lipase required for the reaction (mg).

9. Method for measuring the ratio of immobilized lipase i) Oliver oil (20 g; manufactured by Kanto Chemical, Co., INC.) is mixed with a surfactant (20 g; Adecatol SO-120, manufactured by Asahi Denka Kogyo, K. K.) and pure water (60 ml), and the resulting mixture solution is designated "substrate in emulsion".

ii) To the substrate (25 ml) is added pure water (10 ml) for preheating at 37° C. for 10 minutes.

iii) To the substrate is added an aqueous enzyme solution (0.1 ml) to be used for the immobilizing procedure, for reaction at 37° C. for 5 minutes.

iv) To the reaction solution is added ethanol (80 ml) containing acetone at 50% for stirring, to terminate the enzyme reaction.

v) With 50 mM NaOH, a fatty acid freed from the enzyme reaction is titered to determine the amount required for titration.

vi) As a blank, pure water (0.1 ml) is added, instead of the enzyme solution in the above procedure iii), by the same method as described above. The amount required for titration is determined.

vii) The activity of the aqueous lipase solution prior to the immobilizing procedure for decomposing lipid in emulsion (Activity A; U/ml aqueous solution) is determined by the following formula.

$$\text{Lipase hydrolysis activity in emulsion system} = \frac{\Delta V}{5} \times 50 \times \frac{1}{0.1} \times f \quad (12)$$

wherein
ΔV=(amount required for titration of enzyme reaction solution)−(amount for titration of blank solution)
f=the factor of 50 mM—NaOH.

viii) The activity of the filtrate for decomposing lipid in emulsion after the immobilizing procedure (Activity B; U/ml aqueous solution) is determined in the same manner as described in vii).

ix) From A and B determined in the above vii) and viii), the immobilizing ratio C is determined by the following formula.

$$\text{Immobilizing ratio } C = \frac{(A - B)}{A} \quad (13)$$

10. Method for measuring the ratio of expressed activity i) The weight of the lipase used in the immobilization procedure described in "the method 4" is defined as D (mg). Alternatively, the dry weight of the immobilized lipase is defined as E (mg).

ii) Based on the lipid hydrolysis activity of free lipase (F U/mg) determined by the method described in "the method 5" and the lipid hydrolysis activity of immobilized lipase (G U/mg) determined by the method described in "the method 6", the ratio of expressed activity of the lipid hydrolysis activity is calculated by the following formula.

$$\text{The ratio of expressed activity of lipid (monolaurin) hydrolysis activity (\%)} = \frac{G}{F} \times \frac{E}{D} \times \frac{1}{C} \times 100 \quad (14)$$

iii) Based on the ester exchange activity of free lipase (H U/mg) determined by the method described in "the method 7" and the ester exchange activity of immobilized lipase (I U/mg) determined by the method described in "the method 8", the ratio of expressed ester exchange activity is calculated by the following formula.

$$\text{The ratio of expressed ester exchange acitvity (\%)} = \frac{I}{H} \times \frac{E}{D} \times \frac{1}{C} \times 100 \quad (15)$$

EXAMPLE 6

Chitosan (1200 g) having a deacetylation degree of 80% (the average molecular weight per pyranose ring residue of the chitosan is 169.5) and an average molecular weight of 60,000 was dissolved in an aqueous 3.5% acetate solution (18,800 g). The aqueous solution was dropped into a solidifying solution composed of 7% sodium hydroxide, 20% ethanol and 73% water to solidify and regenerate chitosan into porous material in particles, followed by washing in water to neutral pH, thereby obtaining the regenerated porous chitosan in particles (10,000 ml in wet state) having an average particle size of 0.1 mm. 100 ml of the regenerated porous chitosan in particles thus obtained was dried, and the resulting dry chitosan was 5,086 g in weight. Therefore, the pyranose ring residue of the chitosan contained in 100 ml of the regenerated porous chitosan in particles was 0.0300 mole.

To 100 ml of the regenerated porous chitosan in particles were added water (100 ml) and the amounts of ethylene glycol diglycidyl ether shown in Table 2 (corresponding to 87.13 epoxy equivalents), for cross-linking reaction at 60° C. for 1 hour. After the termination of the reaction, the products were washed in water to obtain 6 samples of regenerated porous chitosan in particles, ie. F, G, H, I, J and K. Each of the samples was 100 ml in volume. The amount of ethylene glycol diglycidyl ether introduced was measured, and the results are shown in Table 2.

TABLE 2

| Samples | Ethylene glycol diglycidyl ether charged | Ethylene glycol diglycidyl ether unreacted | Introduced amount per pyranose ring residue of chirosan |
| --- | --- | --- | --- |
| F | 0.052 g | 0.007 g | 0.009 mole |
| G | 0.261 | 0.046 | 0.041 |
| H | 0.523 | 0.117 | 0.078 |
| I | 2.613 | 0.953 | 0.317 |
| J | 5.225 | 3.381 | 0.353 |
| K | 10.451 | 8.163 | 0.438 |

The water contained in each of the cross-linked regenerated porous chitosan in particles was sufficiently removed with dimethylacetamide. To 100 ml each of the cross-linked regenerated porous chitosan in particles were added dimethylformamide (100 ml), stearoyl chloride (1.524 g) and triethylamine (0.506 g). The concentrations of stearoyl chloride and triethylamine were 50 mmol/liter, individually.

The resulting mixture solution was stirred at 25° C. for 18 hours. After removing the remaining reaction solution, the product was washed with dimethylformamide. Then, dimethylformamide was removed with pure water to obtain carriers F', G', H', I', J' and K'. By thermolysis gas chromatography, the amount of stearic acid introduced was measured per pyranose ring residue of the chitosan. The results are shown in Table 3.

TABLE 3

| Carrier | Amount introduced per pyranose ring residue of the chitosan |
| --- | --- |
| F' | 0.13 mole |
| G' | 0.19 |
| H' | 0.17 |
| I' | 0.19 |
| J' | 0.15 |
| K' | 0.14 |

Onto each of the carriers was immobilized lipase from Chromobacterium biscosm (manufactured by Asahi Chemical Industry Co., Ltd., Type T-01), under the conditions that the given concentration described in the test method "4. Method for preparing immobilized lipase" should be set at 20 mg/ml. Thus, 6 species of immobilized lipase, ie F", G", H", I", J", and K" were generated. Table 4 shows the immobilized enzyme activity, expressed enzyme activity and ratio of immobilized enzyme activity to expressed enzyme activity for these lipase species.

TABLE 4

| Immobilized lipase | Ester exchange activity | | | Lipid hydrolysis activity | | |
|---|---|---|---|---|---|---|
| | Immobilized activity (U/mg) | Expressed activity (U/mg) | Ratio of immobilized activity to expressed activity (%) | Immobilized activity (U/mg) | Expressed activity (U/mg) | Ratio of immobilized activity to expressed activity (%) |
| F" | 0.00267 | 0.313 | 11700 | 2.12 | 0.819 | 38.6 |
| G" | 0.00272 | 0.410 | 15100 | 2.12 | 1.080 | 50.9 |
| H" | 0.00269 | 0.433 | 16100 | 2.13 | 1.127 | 52.9 |
| I" | 0.00265 | 0.350 | 13200 | 2.14 | 0.918 | 42.9 |
| J" | 0.00263 | 0.271 | 10300 | 2.18 | 0.714 | 32.8 |
| K" | 0.00264 | 0.170 | 6400 | 2.14 | 0.449 | 21.0 |

As clearly shown in the results, the ratio of immobilized enzyme activity to expressed enzyme activity of the lipid hydrolysis activity and ester exchange activity of the immobilized lipase species were very high preferably, when the amount of an aliphatic polyalcohol glycidyl ether introduced was 0.01 to 0.4 mole to 1 mole of the pyranose ring residue of the chitosan carrier. Herein, the shrinkage of F" was observed when used in organic solvents. Thus, F" is inappropriate for use.

EXAMPLE 7

To the regenerated porous chitosan in particles (800 ml) in the same manner as in Example 6 were added water (800 ml) and ethylene glycol diglycidyl ether (4.184 g) for cross-linking reaction at 60° C. for 1 hour. After the completion of the reaction, the product was washed in water to obtain cross-linked regenerated porous chitosan in particles (800 ml). The amount of ethylene glycol diglycidyl ether introduced was 0.078 mole.

The water contained in the cross-linked regenerated porous chitosan in particles was sufficiently removed with dimethylacetamide. To eight samples of the cross-linked regenerated porous chitosan in particles (100 ml), ie. L, M, N, O, P, Q, R, and S, were added dimethylformamide (100 ml) and stearoyl chloride and triethylamine, both being at the amounts shown in Table 5 (the individual concentrations of stearoyl chloride and triethylamine then were as shown in Table 5), and the individual mixture solutions were stirred at 40° C. for 10 hours.

TABLE 5

| Samples | Stearoyl chloride | Triethylamine | Concentrations |
|---|---|---|---|
| L | 0.308 g | 0.101 g | 10 mmol/liter |
| M | 0.513 | 0.152 | 15 |
| N | 0.762 | 0.253 | 25 |
| O | 1.523 | 0.506 | 50 |
| P | 2.272 | 0.759 | 75 |
| Q | 4.544 | 1.518 | 150 |
| R | 7.615 | 2.530 | 250 |
| S | 10.780 | 3.535 | 350 |

After removing the remaining reaction solution, the products were washed with dimethylformamide, followed by removing dimethylacetoamide with pure water to obtain carriers L', M', N', O', P', Q', R', and S'. The results of the analysis of the individual carriers by FT-IR are shown in FIGS. 5, 6, 7, 8, 9, 10, 11, and 12. It was confirmed that the absorption of methylene at 2849 $cm^{-1}$ and 2919 $cm^{-1}$ and the absorption of ester at 1738 $cm^{-1}$ were increased to indicate that the stearoyl was introduced. By thermolysis gas chromatography, the amount of stearic acid introduced was measured per 1 mole of the pyranose ring residue of the chitosan carrier. The results are shown in Table 6.

TABLE 6

| Carrier | Amount introduced per pyranose ring residue of the chitosan |
|---|---|
| L' | 0.03 mole |
| M' | 0.05 |
| N' | 0.08 |
| O' | 0.18 |
| P' | 0.28 |
| Q' | 0.56 |
| R' | 0.93 |
| S' | 1.20 |

Onto each of the carriers was immobilized lipase from Chromobacterium biscosm (manufactured by Asahi Chemical Industry Co., Ltd., Type T-01) in the same manner as in Example 6. Then, immobilized lipase species, ie L", M", N", O", P", Q", R" and S", were generated. Table 7 shows the immobilized enzyme activity, expressed enzyme activity and the ratio of immobilized enzyme activity to expressed enzyme activity of these lipase species.

TABLE 7

| Immobilized lipase | Ester exchange activity | | | Lipid hydrolysis activity | | |
|---|---|---|---|---|---|---|
| | Immobilized activity (U/mg) | Expressed activity (U/mg) | Ratio of immobilized activity to expressed activity (%) | Immobilized activity (U/mg) | Expressed activity (U/mg) | Ratio of immobilized activity to expressed activity (%) |
| L" | 0.0048 | 0.080 | 1700 | 3.79 | 0.239 | 6.3 |
| M" | 0.0043 | 0.148 | 3400 | 3.25 | 0.420 | 12.9 |
| N" | 0.0036 | 0.192 | 5300 | 2.90 | 0.640 | 22.1 |
| O" | 0.0027 | 0.269 | 10000 | 2.12 | 0.703 | 33.2 |
| P" | 0.0022 | 0.265 | 12000 | 1.76 | 0.780 | 44.3 |
| Q" | 0.0015 | 0.289 | 19300 | 1.22 | 0.896 | 73.4 |
| R" | 0.0011 | 0.302 | 27500 | 0.88 | 0.936 | 106.4 |
| S" | 0.0010 | 0.303 | 30300 | 0.85 | 0.940 | 110.6 |

As clearly shown in the results, the ratio of immobilized enzyme activity to expressed enzyme activity of the lipid hydrolysis activity and ester exchange activity of the immobilized lipase species were very high preferably, when the amount of a higher fatty acid introduced was 0.05 to 1 mole to 1 mole of the pyranose ring residue of the chitosan carrier.

EXAMPLE 8

To each 50 ml of the cross-linked regenerated porous chitosan in particles obtained by the same method as in Example 6 was added a solution of octanoyl chloride (C6 in total), lauroyl chloride (C12 in total), stearoyl chloride (C18 in total), palmitoyl chloride (C16 in total) or triethylamine (their concentrations were identically 37.5 mmol/liter; and their weights were 0.610 g, 0.821 g, 1.136 g, and 1.031 g, in this order), individually dissolved in dimethylacetamide (50 ml), for reaction at 40° C. for 15 hours. After removing the remaining reaction solution by filtration, the products were washed with dimethylacetoamide, which was subsequently removed with water. Thus, carriers T, U, V and W were produced. By thermolysis gas chromatography, the amount of a higher fatty acid introduced per 1 mole of the pyranose ring residue of the chitosan carrier was measured, and the results are shown in Table 8.

TABLE 8

| Carrier | Reagent required for introducing a higher fatty acid | Introduced amount per pyranose ring residue of chitosan carrier |
|---|---|---|
| T | Octanoyl chloride | 0.17 mole |
| U | Lauroyl chloride | 0.14 |
| V | Palmitoyl chloride | 0.14 |
| W | Stearoyl chloride | 0.12 |

Onto each of the carriers was immobilized lipase from Chromobacterium biscosm (manufactured by Asahi Chemical Industry Co., Ltd., Type T-01) in the same manner as in Example 6, to obtain immobilized lipase species, ie. T', U', V', and W'. Table 9 shows the immobilized enzyme activity, expressed enzyme activity and ratio of immobilized enzyme activity to expressed enzyme activity.

TABLE 9

| Immobilized lipase | Ester exchange activity | | | Lipid hydrolysis activity | | |
|---|---|---|---|---|---|---|
| | Immobilized activity (U/mg) | Expressed activity (U/mg) | Ratio of immobilized activity to expressed activity (%) | Immobilized activity (U/mg) | Expressed activity (U/mg) | Ratio of immobilized activity to expressed activity (%) |
| T" | 0.0021 | 0.196 | 9300 | 1.96 | 0.627 | 32.0 |
| U" | 0.0028 | 0.268 | 9600 | 2.19 | 0.740 | 33.8 |
| V" | 0.0031 | 0.300 | 9700 | 2.47 | 0.783 | 31.7 |
| W" | 0.0032 | 0.264 | 8300 | 2.56 | 0.883 | 34.5 |

As clearly shown in the results, the immobilized enzyme activity to expressed enzyme activity of the lipid hydrolysis activity and ester exchange activity of the immobilized lipase species were very high preferably, when the total carbon number of a higher fatty acid was in a range of 6 to 20.

EXAMPLE 9

In the same manner as in Example 7, carrier N' was obtained. To the carrier (5 ml) was added 195,000 U of lipase from Pseudomonas (manufactured by Asahi Chemical Industry Co., Ltd., Type T-18) which was preliminarily dissolved in 10 mM phosphate buffer solution, pH 7.5 (25 ml) for stirring for 1 hour. After sufficiently washing the product with 10 mM phosphate buffer solution, glutaraldehyde was added to 0.2%, for stirring at 37° C. for 30 minutes to effect cross-linking. By filtration, wet immobilized lipase was collected to obtain immobilized lipase in dry state by the same method as in Example 6. The immobilized activity, lipid hydrolysis activity and ester exchange activity thereof were measured, and the results are shown in Table 10.

TABLE 10

| Ester exchange activity | | | Lipid hydrolysis activity | | |
|---|---|---|---|---|---|
| Immobilized activity (U/mg) | Expressed activity (U/mg) | Ratio of immobilized activity to expressed activity (%) | Immobilized activity (U/mg) | Expressed activity (U/mg) | Ratio of immobilized activity to expressed activity (%) |
| 0.0016 | 0.135 | 8400 | 1.42 | 0.371 | 26.1 |

As apparently shown in the results, excellent lipid hydrolysis activity and ester exchange activity were brought about by the use of lipase from Pseudomonas.

EXAMPLE 10

By modifying the concentration of lipase as shown in Table 11, lipase from Chromobacterium biscosm (Asahi Chemical Industry Co., Ltd.; T-01) was immobilized onto the generated carrier N' (1 g in wet weight), by the same method as in Example 7. By the same procedure as in Example 6, dry immobilized lipase was prepared to measure the expressed enzyme activity and the ratio immobilized enzyme activity to expressed activity for ester exchange reaction and lipid (monolaurin) hydrolysis reaction. The results are shown in Table 11. Also, 50 mg of the dry immobilized lipase was weighed and suspended in n-hexane (2 ml), for stirring at 37° C. for 18 hours. Subsequently, the suspension was filtered through a glass filter, to recover immobilized lipase. Then, the ester exchange activity of the immobilized lipase was measured, to calculate the ratio of remained activity after suspension in hexane by the following formula. The results are shown in Table 11.

Ratio of remained activity (%) = (16)

$$\frac{\text{(Ester exchange activity of a sample suspended in hexane and treated at 37° C.)}}{\text{(ester exchange activity of a sample never suspended)}} \times 100$$

The activity was increased as the amount of lipase immobilized was higher. Particularly in the range of 0.01 to 1.5 U/mg of the lipid hydrolysis activity, the activity increased in proportion to the amount of lipase immobilized, and the ratio of remained activity was nearly constant. When the lipid hydrolysis activity was above 1.6 U/mg, the activity was not in proportion to the amount of lipase immobilized, however, the ratio of remained activity decreased.

When the lipid hydrolysis activity is preferably in a range of 0.01 to 2 U/mg, more preferably in a range of 0.1 to 1.5 U/mg, activity yield and the ratio of remaining activity are distinctively excellent.

As is apparently shown in the description of the Examples, the present invention is to provide an enzyme immobilizing carrier produced by dissolving low-molecular weight chitosan in an aqueous acid solution and dropping the solution into a basic solution to produce regenerated porous chitosan in particles, reacting the regenerated porous chitosan in particles with the glycidyl ether of an aliphatic polyalcohol, and reacting further the resulting chitosan with the acid halide or acid anhydride of a higher fatty acid in a polar solvent. The enzyme immobilizing carrier in accordance with the present invention has a higher immobilized enzyme activity and expressed activity for the enzyme requiring hydrophobicity for the immobilizing carrier.

Furthermore, the immobilized lipase in accordance with the present invention has a lipid hydrolysis activity of 0.01 to 2 U/mg per dry weight of the immobilized lipase, and is produced by dissolving low-molecular weight chitosan in an aqueous acid solution and dropping the solution into a basic solution, thereby producing regenerated porous chitosan in particles, introducing the glycidyl ether of an aliphatic

TABLE 11

| | Ester exchange activity | | | Lipid hydrolysis activity | |
|---|---|---|---|---|---|
| Lipase concentration (mg/ml) | Expressed enzyme activity (U/mg) | Ratio of expressed activity (%) | Ratio of remained activity (%) | Expressed enzyme activity (U/mg) | Ratio of expressed activity (%) |
| 0.06 mg/ml | 0.0006 | 9800 | 53.9 | 0.0015 | 36.5 |
| 0.2 | 0.003 | 14600 | 60.3 | 0.009 | 55.7 |
| 0.6 | 0.005 | 15900 | 76.0 | 0.030 | 59.9 |
| 2 | 0.038 | 16600 | 99.4 | 0.103 | 62.5 |
| 6 | 0.098 | 15900 | 98.1 | 0.297 | 60.6 |
| 20 | 0.343 | 18000 | 100.2 | 0.969 | 63.7 |
| 30 | 0.458 | 16400 | 106.3 | 1.387 | 61.9 |
| 40 | 0.526 | 14200 | 98.6 | 1.580 | 53.4 |
| 60 | 0.566 | 10300 | 99.8 | 1.695 | 38.5 |

As clearly shown in the results, the lipid hydrolysis activity was above 0.01 U/mg after storage in an organic solvent. Therefore, the ratio of remained activity was high. At greater than 0.1 U/mg, extremely stable immobilized lipase was prepared.

polyalcohol into the regenerated porous chitosan in particles at a ratio of 0.01 to 0.4 mole per 1 mole of the pyranose ring residue of the chitosan, and also introducing the acid halide or acid anhydride of a higher fatty acid of C6 to C20 in total at a ratio of 0.05 to 1 mole per 1 mole of the pyranose ring residue of the chitosan, wherein the lipase is immobilized via covalent bonding. The immobilized lipase with a lipid hydrolysis activity of 0.01 to 2 U/mg per dry weight of to the immobilized lipase has an excellent catalytic activity in the hydrolysis, synthesis or exchange reaction of ester bonds in an organic solvent. More specifically, the immobilized lipase has an excellent effect on the organic synthesis via the exchange reaction of a variety of esters, such as the capability of asymmetric synthesis at a far higher efficiency than free lipase enzyme in powder and conventional immobilized lipase.

What is claimed is:

1. An immobilized lipase produced by dissolving low-molecular weight chitosan in an aqueous acid solution and dropping the solution into a basic solution, thereby producing regenerated porous chitosan in particles, reacting a glycidyl ether of an aliphatic polyalcohol with the regenerated porous chitosan in particles at a ratio of 0.01 to 0.4 mole glycidyl ether per 1 mole of the pyranose ring residue of the chitosan to crosslink the regenerated porous chitosan, reacting an acid halide or acid anhydride of a higher fatty acid of C6 to C20 in total at a ratio of 0.05 to 1 mole acid halide or acid anhydride per 1 mole of the pyranose ring residue of the chitosan to obtain an enzyme immobilizing carrier, and reacting a lipase and a polyfunctional cross-linking agent with the enzyme immobilizing carrier to covalently bind the lipase to the enzyme immobilizing carrier to obtain the immobilized lipase.

2. An immobilized lipase as claimed in claim 1, wherein said glycidyl ether is ethylene glycol diglycidyl ether.

3. An immobilized lipase as claimed in claim 1, wherein said acid halide of a higher fatty acid is stearoyl chloride.

4. An immobilized lipase as claimed in claim 1, wherein said acid anhydride of a higher fatty acid is myristic anhydride.

5. An immobilized lipase as claimed in claim 1, wherein said acid halide of a higher fatty acid is octanoyl chloride.

6. An immobilized lipase as claimed in claim 1, wherein said acid halide of a higher fatty acid is lauroyl chloride.

7. An immobilized lipase as claimed in claim 1, wherein said acid halide of a higher fatty acid is palmitoyl chloride.

8. An immobilized lipase as claimed in claim 1, wherein said polyfunctional cross-linking agent is glutaraldehyde.

9. An immobilized lipase produced by dissolving low-molecular weight chitosan in an aqueous acid solution and dropping the solution into a basic solution, thereby producing regenerated porous chitosan in particles, reacting a glycidyl ether of an aliphatic polyalcohol selected from the group consisting of ethylene glycol diglycidyl ether or polyethylene glycol diglycidyl ether, having a dimethylene ether repeating number of 1 to 22, polypropylene glycol diglycidyl ether having a propylene ether repeating number of 1 to 66 and glycerol polyglycidyl ether having 2 to 3 glycidyl ethers, with the regenerated porous chitosan in particles at a ratio of 0.01 to 0.4 mole glycidyl ether per 1 mole of the pyranose ring residue of the chitosan to crosslink the regenerated porous chitosan, reacting an acid halide of a higher fatty acid selected from the group consisting of lauroyl chloride, myristoyl chloride, palmitoyl chloride, stearoyl chloride, and oleyl chloride, or an acid anhydride of a higher fatty acid of C6 to C20 selected from the group consisting of lauric anhydride, myristic anhydride, palmitic anhydride, stearic anhydride, octanoyl chloride and oleic anhydride, at a ratio of 0.05 to 1 mole acid halide or acid anhydride per 1 mole of the pyranose ring residue of the chitosan to obtain an enzyme immobilizing carrier, and reacting a lipase and a polyfunctional cross-linking agent with the enzyme immobilizing carrier to covalently bind the lipase to the enzyme immobilizing carrier to obtain the immobilized lipase.

* * * * *